United States Patent
Seitz et al.

(10) Patent No.: US 9,206,218 B2
(45) Date of Patent: Dec. 8, 2015

(54) PROBES COMPRISING FLUORESCENT ARTIFICIAL NUCLEOBASES AND USE THEREOF FOR DETECTION OF SINGLE BASE ALTERATION

(75) Inventors: Oliver Seitz, Berlin (DE); Lucas Bethge, Potsdam (DE); Sven Hainke, Berlin (DE)

(73) Assignee: HUMBOLDT-UNIVERSITAT ZU BERLIN, Berlin (DE)

( * ) Notice: Subject to any disclaimer, the term of this patent is extended or adjusted under 35 U.S.C. 154(b) by 458 days.

(21) Appl. No.: 13/394,729

(22) PCT Filed: Sep. 8, 2010

(86) PCT No.: PCT/EP2010/063156
§ 371 (c)(1),
(2), (4) Date: Apr. 30, 2012

(87) PCT Pub. No.: WO2011/029835
PCT Pub. Date: Mar. 17, 2011

(65) Prior Publication Data
US 2012/0208178 A1 Aug. 16, 2012

(30) Foreign Application Priority Data

Sep. 8, 2009 (EP) .................... 09169747

(51) Int. Cl.
| | |
|---|---|
| C07H 21/02 | (2006.01) |
| C07H 21/04 | (2006.01) |
| C07H 19/04 | (2006.01) |
| C12Q 1/68 | (2006.01) |
| B01L 3/00 | (2006.01) |
| C07H 21/00 | (2006.01) |

(52) U.S. Cl.
CPC .............. *C07H 21/00* (2013.01); *C12Q 1/6813* (2013.01); *C12Q 1/6869* (2013.01); *C12Q 2525/117* (2013.01)

(58) Field of Classification Search
CPC .... C07H 21/00; C12Q 1/6813; C12Q 1/6869; C12Q 2525/117
USPC ............... 536/23.1, 24.3, 25.3, 26.6; 435/6.1; 422/430
See application file for complete search history.

(56) References Cited

U.S. PATENT DOCUMENTS

2010/0112561 A1* 5/2010 Lutz et al. .................. 435/6

OTHER PUBLICATIONS

Moran, Nina et al: "Detection of a single DNA base-pair mismatch using an anthracene-tagged fluorescent probe", Chemical Communications (Cambridge, United Kingdom), vol. 48, pp. 5003-5005, 2006.

Kohler O. et al: "Forced intercalation probes (FIT probes): thiazole orange as a fluorescent base in peptide nucleic acids for homogeneous single-nucleotide-polymorphism detection", Chembiochem—A European Journal of Chemical Biology, vol. 6, No. I, Jan. 1, 2005, pp. 69-77.

(Continued)

*Primary Examiner* — Jezia Riley
(74) *Attorney, Agent, or Firm* — Pearl Cohen Zedek Latzer Baratz LLP

(57) ABSTRACT

The present invention relates to forced intercalation probes (FIT-probes) comprising at least one nucleoside analog which comprises at least a fluorescent artificial nucleobase directly bound to a carbon of a modified sugar moiety wherein said modified sugar moiety is a carba-sugar or an amino acid nucleic acid (AANA). Thereby the nucleoside analog is incorporated into DNA or RNA in the place of a single native base.

19 Claims, 7 Drawing Sheets

(56) References Cited

OTHER PUBLICATIONS

Szemzo, A. et al: "First synthesis of carbocyclic 01 igothymidylates", Tetrahedron Letters, vol. 31, No. 10, pp. 1463-1466, 1990.

Ueno, Y. et al.: "Nucleosides and Nucleotides. 204. Synthesis of oligodeoxynucleotides containing 6'-alpha-[N(aminoalkyl)carbamoyloxy]-carbocyclic-thymidines and the thermal stability of the duplexes and their nuclease-resistance properties", Bioconjugate Chemistry, vol. 11, No. 6, 2000, pp. 933-940.

Altmann K-H et al: "6'-Carbon-Substituted Carbocyclic Analogs of 2'-Deoxyribonucleosides—Synthesis and Effect on DNA/RNA Duplex Stability", Tetrahedron, vol. 52, No. 39, Jan. 1, 1996, pp. 12699-12722.

Ahn et al: "Synthesis of Cyclopentane Amide DNA (cpa-DNA) and Its Pairing Properties", Journal of Organic Chemistry, vol. 68, No. 20, Jan. 1, 2003, pp. 7693-7699.

International Search Report for International Application No. PCT/EP2010/063156 dated Jun. 24, 2011.

\* cited by examiner

SEQUENCE LISTING

```
<160> NUMBER OF SEQ ID NOS: 34

<210> SEQ ID NO 1
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (L)-Serinol(thiazole orange)

<400> SEQUENCE: 1
gccgtanata gccg                                                     14

<210> SEQ ID NO 2
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (L)-Serinol(thiazole orange)

<400> SEQUENCE: 2
gccgttntta gccg                                                     14

<210> SEQ ID NO 3
<211> LENGTH: 14
<212> TYPE: DNA
<213> ORGANISM: Artificial Sequence
```

```
<220> FEATURE:
<223> OTHER INFORMATION: probe
<220> FEATURE:
<221> NAME/KEY: misc_feature
<222> LOCATION: (7)..(7)
<223> OTHER INFORMATION: (L)-Serinol(thiazole orange)

<400> SEQUENCE: 3
gccgtcncta gccg                                                       14

<210> SEQ ID NO 4
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (L)-Serinol(thiazole orange)

<400> SEQUENCE: 4
gccgtgngta gccg                                                       14

<210> SEQ ID NO 5
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (D)-Serinol(thiazole orange)

<400> SEQUENCE: 5
gccgtanata gccg                                                       14

<210> SEQ ID NO 6
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (D)-Serinol(thiazole orange)

<400> SEQUENCE: 6
gccgttntta gccg                                                       14

<210> SEQ ID NO 7
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (D)-Serinol(thiazole orange)

<400> SEQUENCE: 7
gccgtcncta gccg                                                       14

<210> SEQ ID NO 8
<211> LENGTH: 14
<212> TYPE: DNA
```

<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: (D)-Serinol(thiazole orange)

<400> SEQUENCE: 8
gccgtgngta gccg                                                    14

<210> SEQ ID NO 9
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: beta-(D)-Carba-deoxyribose(thiazole orange)

<400> SEQUENCE: 9
gccgtanata gccg                                                    14

<210> SEQ ID NO 10
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: beta-(D)-Carba-deoxyribose(thiazole orange)

<400> SEQUENCE: 10
gccgttntta gccg                                                    14

<210> SEQ ID NO 11
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: beta-(D)-Carba-deoxyribose(thiazole orange)

<400> SEQUENCE: 11
gccgtcncta gccg                                                    14

<210> SEQ ID NO 12
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: beta-(D)-Carba-deoxyribose(thiazole orange)

<400> SEQUENCE: 12
gccgtgngta gccg                                                    14

<210> SEQ ID NO 13
<211> LENGTH: 14

```
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: alpha-(D)-Carba-deoxyribose(thiazole orange)

<400> SEQUENCE: 13
gccgtanata gccg                                                        14

<210> SEQ ID NO 14
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: alpha-(D)-Carba-deoxyribose(thiazole orange)

<400> SEQUENCE: 14
gccgttntta gccg                                                        14

<210> SEQ ID NO 15
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: alpha-(D)-Carba-deoxyribose(thiazole orange)

<400> SEQUENCE: 15
gccgtcncta gccg                                                        14

<210> SEQ ID NO 16
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: alpha-(D)-Carba-deoxyribose(thiazole orange)

<400> SEQUENCE: 16
gccgtgngta gccg                                                        14

<210> SEQ ID NO 17
<211> LENGTH: 14
<212> TYPE: DNA
<213> ORGANISM: Artificial Sequence
<220> FEATURE:
<223> OTHER INFORMATION: target

<400> SEQUENCE: 17
cggctattta cggc                                                        14

<210> SEQ ID NO 18
<211> LENGTH: 14
<212> TYPE: DNA
<213> ORGANISM: Artificial Sequence
<220> FEATURE:
```

```
<223> OTHER INFORMATION: target

<400> SEQUENCE: 18
cggctaataa cggc                                              14

<210> SEQ ID NO 19
<211> LENGTH: 14
<212> TYPE: DNA
<213> ORGANISM: Artificial Sequence
<220> FEATURE:
<223> OTHER INFORMATION: target

<400> SEQUENCE: 19
cggctagtga cggc                                              14

<210> SEQ ID NO 20
<211> LENGTH: 14
<212> TYPE: DNA
<213> ORGANISM: Artificial Sequence
<220> FEATURE:
<223> OTHER INFORMATION: target

<400> SEQUENCE: 20
cggctactca cggc                                              14

<210> SEQ ID NO 21
<211> LENGTH: 13
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: (L)-Serinol(thiazole orange)

<400> SEQUENCE: 21
acaccnacgg cgc                                               13

<210> SEQ ID NO 22
<211> LENGTH: 13
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: (D)-Serinol(thiazole orange)

<400> SEQUENCE: 22
acaccnacgg cgc                                               13

<210> SEQ ID NO 23
<211> LENGTH: 13
<212> TYPE: DNA
<213> ORGANISM: Homo sapiens

<400> SEQUENCE: 23
gcgccgtcgg tgt                                               13

<210> SEQ ID NO 24
<211> LENGTH: 16
<212> TYPE: DNA
```

```
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: alpha-(D)-Carba-deoxyribose(thiazole orange)

<400> SEQUENCE: 24
aaaaatgngg caaata                                                       16

<210> SEQ ID NO 25
<211> LENGTH: 16
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (13)..(13)
<223> OTHER INFORMATION: alpha-(D)-Carba-deoxyribose(thiazole orange)

<400> SEQUENCE: 25
aaaaatgggg canata                                                       16

<210> SEQ ID NO 26
<211> LENGTH: 16
<212> TYPE: RNA
<213> ORGANISM: Bovine respiratory syncytial virus

<400> SEQUENCE: 26
uauuugcccc auuuuu                                                       16

<210> SEQ ID NO 27
<211> LENGTH: 14
<212> TYPE: DNA
<213> ORGANISM: Artificial Sequence
<220> FEATURE:
<223> OTHER INFORMATION: probe

<400> SEQUENCE: 27
gccgtaaata gccg                                                         14

<210> SEQ ID NO 28
<211> LENGTH: 14
<212> TYPE: DNA
<213> ORGANISM: Artificial Sequence
<220> FEATURE:
<223> OTHER INFORMATION: target

<400> SEQUENCE: 28
cggctattaa cggc                                                         14

<210> SEQ ID NO 29
<211> LENGTH: 14
<212> TYPE: DNA
<213> ORGANISM: Artificial Sequence
<220> FEATURE:
<223> OTHER INFORMATION: target

<400> SEQUENCE: 29
cggctattga cggc                                                         14

<210> SEQ ID NO 30
```

```
<211> LENGTH: 14
<212> TYPE: DNA
<213> ORGANISM: Artificial Sequence
<220> FEATURE:
<223> OTHER INFORMATION: target

<400> SEQUENCE: 30
cggctattca cggc                                                       14

<210> SEQ ID NO 31
<211> LENGTH: 14
<212> TYPE: DNA
<213> ORGANISM: Artificial Sequence
<220> FEATURE:
<223> OTHER INFORMATION: target

<400> SEQUENCE: 31
cggctaatta cggc                                                       14

<210> SEQ ID NO 32
<211> LENGTH: 14
<212> TYPE: DNA
<213> ORGANISM: Artificial Sequence
<220> FEATURE:
<223> OTHER INFORMATION: target

<400> SEQUENCE: 32
cggctaatga cggc                                                       14

<210> SEQ ID NO 33
<211> LENGTH: 14
<212> TYPE: DNA
<213> ORGANISM: Artificial Sequence
<220> FEATURE:
<223> OTHER INFORMATION: target

<400> SEQUENCE: 33
cggctaatca cggc                                                       14

<210> SEQ ID NO 34
<211> LENGTH: 13
<212> TYPE: DNA
<213> ORGANISM: Homo sapiens

<400> SEQUENCE: 34
gcgccggcgg tgt                                                        13
```

PROBES COMPRISING FLUORESCENT ARTIFICIAL NUCLEOBASES AND USE THEREOF FOR DETECTION OF SINGLE BASE ALTERATION

CROSS-REFERENCE TO RELATED APPLICATIONS

This application is a National Phase Application of PCT International Application No. PCT/EP2010/063156, International Filing Date Sep. 8, 2010, claiming priority of European Patent Application No. 09169747A, filed Sep. 8, 2009

BACKGROUND OF THE INVENTION

The present invention relates to forced intercalation probes (FIT-probes) comprising at least one nucleoside analogue which comprises at least a fluorescent artificial nucleobase directly bound to a carbon of a modified sugar moiety wherein said modified sugar moiety is a carba-sugar or an amino acid nucleic acid (AANA). Thereby the nucleoside analogue is incorporated into DNA or RNA in the place of a single native base.

As such, FIT-probes may be employed in a large number of applications including genetic diagnostics, disease predisposition, pharmacogenetics and pathogen detection. The FIT-probes exhibit a simplistic mode of action and are able to detect single base alteration. They further possess few design constraints and show melting peak data which can be interpreted easily. The assay has been demonstrated to function efficiently directly from samples without prior purification of nucleic acids making the probe technology suitable for point-of-care diagnostics.

Variations in the DNA sequences of humans can affect how humans develop diseases and respond to pathogens, chemicals, drugs, vaccines, and other agents. SNPs are also thought to be key enablers in realizing the concept of personalized medicine. However, their greatest importance in biomedical research is for comparing regions of the genome between cohorts (such as with matched cohorts with and without a disease).

The polymerase chain reaction (PCR) by using hybridization probes is an extremely versatile technique for copying and qualitative and quantitative detection of DNA. In brief, PCR allows a single DNA sequence to be copied (millions of times), or altered in predetermined ways. Diagnostics for genetic diseases are run and sequence analysis of DNA are carried out by hybridization of RNA transcripts with oligonucleotide array microchips.

A hybridization probe is a fragment of DNA or RNA of variable length (usually 100-1000 bases long), which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labelled probe is first denatured (by heating or under alkaline conditions) into single stranded DNA and then hybridized to the target DNA (Southern blotting) or RNA (northern blotting) immobilized on a membrane or in situ.

DNA sequences or RNA transcripts that have moderate to high sequence similarity to the probe are then detected by visualizing the hybridized probe via imaging techniques. Detection of sequences with moderate or high similarity depends on how stringent the hybridization conditions were applied—high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in DNA microarrays refer to DNA covalently attached to an inert surface, such as coated glass slides or gene chips, and to which a mobile cDNA target is hybridized. Depending on the method the probe may be synthesized via phosphoamidite technology or generated and labelled by PCR amplification.

Fluorescence-labelled DNA probes play an important role in recent development of the detection of single-base alterations. The single-base discrimination in nearly all reported methods is achieved directly or indirectly in the basis of different hybridization efficiency between matched and mismatched target DNA/probe DNA duplexes. However, as far as the detection relies on the hybridization event, such DNA probes have inherent limitations in their selectivity. The differences in the hybridization efficiency vary with sequence context, and often are very small for the detection of a single-base mismatch in long-target DNA.

Methods having only one chromophore are preferred. Known methods are HyBeacon, LightUp-probes, base discriminating fluorosides (BDF) and FIT-probes.

HyBeacon probes provide a homogeneous method of ultrarapid sequence analysis that allows samples to be genotyped in a short time. These fluorescent probes are capable of reliably detecting specific DNA targets and discriminating closely related sequences, including those containing single nucleotide polymorphisms (SNPs). The design of the HyBeacon probe is characterized by a fluorescent derivative anchored on a nucleobase. The fluorescence of the chromophore is quenched in the unlinked state by batch with the nucleobase. In the case of hybridization with the target-DNA the quenching is decreased. However, selectivity of HyBeacon probes is limited.

The light-up probe is a recently developed probe for monitoring PCR amplification in real time. The design is characterized by anchoring of an intercalation dye at the end of an oligonucleotide over a flexible linker. It is a peptide nucleic acid (PNA) coupled to an asymmetric cyanine dye that becomes fluorescent upon binding nucleic acids. The light-up probe is used to monitor product accumulation in regular three steps PCR. It is designed to bind target DNA at annealing temperature, where the fluorescent signal is recorded, and to dissociate at elongation temperature. The differentiation of single mismatched complex is only possible by stringent hybridisation conditions.

A further strategy to discriminate single-base alterations are base-discriminating fluorescent (BDF) oligonucleotides probes. The BDF probes containing these fluorescent nucleosides selectively emit fluorescence only when the base opposite the BDF base is a target base. Oligonucleotides containing these BDF nucleosides act as effective reporter probes for homogeneous SNP typing of DNA samples. It is disadvantageous that the BDF probes are not universal usable or that they demonstrate the presence of a perfect complementary target-DNA by decreasing of the fluorescence.

Forced intercalation probes (FIT-probes) are peptide nucleic acid-based probes (PNA) in which the thiazole orange dye replaces a canonical nucleobase (WO 2006/072368A2). FIT-probes are used in homogenous DNA detection. The analysis is based on sequence-specific binding of the FIT-probe with DNA. FIG. 1A-shows the principle of detection. Binding of the FIT-probe places thiazole orange in the interior of the formed duplex. The intercalation of thiazole orange between nucleobases of the formed probe-target duplex restricts the torsional flexibility of the two heterocyclic ring systems (FIG. 1B). As a result, FIT probes show strong enhancements of fluorescence upon hybridization (FIG. 1A1). A less remarkable attenuation of fluorescence is observed when forcing thiazole orange to intercalate next to a mismatched base pair (FIG. 1A2). This base specificity of fluorescence signalling, which adds to the specificity of probe-target recognition, allows the detection of single base mutations even at non-stringent hybridization conditions. However, FIT-probes based on PNA show a high lipophilic character in comparison to DNA. Due to said differences PNA probes show undesirable high adhesion. Further, it is not possible to modify PNA chemically or with enzymes in the great diversity of DNA and the automated DNA synthesis and analysis is not compatible with the PNA systems.

Alternative FIT-probes which are based on the normal DNA sugar backbone are difficult to synthesize. To stabilize the fluorescent dye as base analogue in said probes long and flexible linker groups, such as substituted or unsubstituted alkyl chains, have to be included between the C1-atom of the sugar ring and the fluorescent dye. Furthermore, these probes show only a very weak signal intensity which is not sufficient to detect single base mutations effectively.

Thus, it is the object of the present invention to provide FIT-probes which show a strong fluorescence signal so that single base mutations can be detected reliably. It should be further possible to synthesize and analyze said FIT-probes by the automated systems usually used for DNA or RNA.

SUMMARY OF THE INVENTION

The present invention relates to a probe comprising at least one nucleoside analogue having the formula

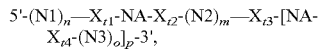

5'-(N1)$_n$—X$_{t1}$-NA-X$_{t2}$-(N2)$_m$—X$_{t3}$-[NA-X$_{t4}$-(N3)$_o$]$_p$-3', wherein
N1, N2, N3 is identical or different being guanosine, cytidine, adenosine, thymidine, uracidine, inosine or a modification thereof,
NA is a nucleoside analogue being a fluorescent artificial nucleobase directly bound to a carbon of a modified sugar moiety wherein said modified sugar moiety is a carba-sugar or an amino acid nucleic acid (AANA),
n is an integer from 0 to 100,
m is an integer from 0 to 100, is an integer from 0 to 100,
p is an integer from 0 to 20
X is a linker group containing at least one phosphor atom and t1, t2, t3, t4 is an integer from 0 to 5.

It was surprisingly found by the inventors that probes having said formula are suitable for detection of single base mutations. Said probes show an excellent change in fluorescence intensity upon hybridizing to the complementary or single mismatch strand. Thereby, perfect-match and mismatch hybridization can be distinguished clearly because perfect-match hybridization results in higher fluorescence signals.

Advantageously, the probes according to the present invention can be synthesized automatically using the standard DNA synthesizers and are accessible to many chemical or enzymatic modification.

The probes according to the invention comprise at least one nucleoside analogue. In the nucleoside analogue the fluorescent dye is bound instead of the canonical bases to the modified sugar moiety. To achieve the requested fluorescence intensity, the number of bonds between the fluorescent dye and the modified sugar is reduced to a minimum, i.e. the fluorescent dye is bound without a linker group. In the most preferred embodiment of the invention the bond between the fluorescent dye and the modified sugar moiety is a direct carbon-nitrogen bond.

Carba-sugars are suitable modified sugar moieties according to the present invention. Carba-sugars are cyclic sugar compounds, wherein the endocyclic oxygen of the sugar is replaced by a carbon atom. Suitable carba-sugars are carba-pentoses, in particular carba-D-/L-ribose, carba-D-/L-arabinose, carba-D-/L-xylose, carba-D-/L-lyxose, carba-hexoses, such as carba-pyranoses or carba-furanoses, in particular carba-D-/L-allose, carba-D-/L-altrose, carba-D-/L-glucose, carba-D-/L-mannose, carba-D-/L-gulose, carba-D-/L-idose, carba-D-/L-galactose, carba-D-/L-talose, carba-D-/L-fructose, carba-heptanoses or modifications thereof. A preferred modification according to the invention is the deoxy-modification, for example carba-D-/L-deoxyribose, carba-D-/L-deoxyarabinose or carba-D-/L-deoxyfructose.

Advantageously carba-sugars can be synthesized easily and build a very stable bond to the fluorescent base analogue. According to the invention the preferred carba-sugars are carba-furanoses, preferably carba-D-ribose and carba-D-deoxyribose which are isoster compared to the natural DNA. It is a further advantage of these modified sugars that the number of bonds between the backbone and the artificial base is identical to the number of bonds in the natural nucleoside. Formula I shows the general chemical structure of a preferred carba-furanose according to the present invention.

wherein Z is a CH$_2$,— group, a CHR-group or a CR$_2$-group, whereby R is identical or different being an organic residue, in particular a substituted or unsubstituted C$_1$-C$_6$ alkyl group, a substituted or unsubstituted phenyl group or a substituted or unsubstituted amino group, wherein the substituent is an amino-group, a C$_1$-C$_6$ alkyl group or an element of the 5$^{th}$ or 6$^{th}$ main group of the periodic table, preferably O or S, and most preferred Z is a CH$_2$-group.

R$^1$, R$^2$, R$^3$ and R$^4$ are identical or different being hydrogen, a hydroxyl-group, a halogen, a cyano group, an azido group, preferably an azido alkyl group, a substituted or unsubstituted C$_1$- to C$_6$-alkyl group, a substituted or unsubstituted phenyl group, a substituted or unsubstituted amino group, wherein the substituent is an amino-group, a C$_1$-C$_6$ alkyl group or an element of the 5$^{th}$ or 6$^{th}$ main group of the periodic table, preferably O or S, and most preferred R$^1$, R$^2$, R$^3$ and R$^4$ are a hydrogen, a fluoro group, a hydroxyl group, an amino group, a dimethyl amino group, a diethyl amino group, a carboxy group or a O-hydroxyalkyl group, alkenyl group, an alkinyl group, preferably a terminal alkinyl group and R$^5$ is a hydroxyl group or a substituted or unsubstituted amino- or thio group, wherein the substituent is an amino group, a C$_1$-C$_6$ alkyl group or an element of the 5$^{th}$ or 6$^{th}$ main group of the periodic table, preferably O or S and most preferred R$^5$ is OH. In another embodiment of the invention the linker group X which is located between the nucleosides and the nucleoside analogue is bound to R$^2$ and/or R$^5$.

In a further preferred embodiment the fluorescent artificial nucleobase is linked to the C1 of the carba-sugar in α- or β-configuration. The chemical structure of the most preferred D-deoxyribose is shown in FIG. 2C. The fluorescent base analogue can be bound either in α- or in β-configuration.

Amino acid nucleic acids (AANA) are further suitable modified sugar moieties according to the present invention. FIGS. 2A and B show the general chemical structure of a preferred nucleoside analogue in D- and L-configuration, respectively.

A, B and D are identical or different and represent an element of the 4$^{th}$ main group of the periodic table, preferably carbon, a substituted or unsubstituted C1- to C6-alkyl group, a substituted or unsubstituted phenyl group, a substituted or unsubstituted amino group, wherein the substituent is an amino-group, a $C_1$-$C_6$ alkyl group or an element of the 5$^{th}$ or 6$^{th}$ main group of the periodic table, preferably O or S. In order to achieve a high fluorescence signal in the hybridization assays D is minimized, preferably D is an unsubstituted C1-alkyl group. In a further preferred embodiment A and B are a substituted or an unsubstituted $C_1$-$C_3$-group. Every chiral carbon atom in the AANA results in two different isomeric forms which can be used as modified acyclic sugar moiety according to the present invention. In a more preferred embodiment of the invention the modified sugar moiety being an AANA is D-Serinol, L-Serinol, D-Threoninol, L-Threoninol, D-allo-Threoninol or L-allo-Threoninol, D-iso-Threoninol, L-iso-Threoninol, D-iso-allo-Threoninol or L-iso-allo-Threoninol which are isoster compared to the natural DNA and which can be synthesized easily. Compared to the number of bonds in the natural nucleoside one additional bond is located between the backbone and the artificial base. This backbone structure is very similar to natural DNA and hybridisation is not changed by the additional bond. It is a further advantage that the ANAA monomers according to the present invention can be incorporated into DNA or RNA by means of automated DNA or RNA synthesis.

The probes according to the present invention comprise besides the artificial nucleoside further nucleosides. Suitable nucleosides (N1, N2, N3) are the natural, i.e. canonical nucleosides guanosine, cytidine, adenosine, thymidine or uracidine, as well as nucleoside analogues such as inosine. According to the invention also commonly known modifications of nucleosides can be used for synthesizing the probe according to the invention. Examples for modifications of nucleosides are methylated nucleosides, i.e. nucleosides methylated at C1, C2, C3 and/or C5, di-methylated nucleosides, such as 2,2-dimethylpurine, 2,2-dimethylpyrimidine, 7'-deazopurines, 5'-propinyl-pyrimidines, 5'-aziridinylcytidine, 4-acetylcytidine, 5-fluorouracidine, 5-bromouracidine, 5-carboxymethylaminomethyl-2-thiouracidine, 5-carboxymethyl-aminomethyluracidine, N6-isopentenyladenosine, pseudouracidine, 1-methylpseudouracidine, 5-pentynyluracidine or 2,6-diaminopurine. Every further modified nucleoside which is usually known by the skilled person can be used as nucleoside in the probe according to the invention. The nucleosides according to the invention can be combined in any sequences and length within the range.

According to the present invention the nucleosides and/or the artificial nucleoside are connected by a linker group X containing at least one phosphor atom. In a preferred embodiment the linker group X is a mono-, di-, triphosphate, a mono-, di-, triphosphonate, a methyl phosphonate, a phosphorothioate or a phosphorodithioate, a phosphorselenoate, an amide, a phosphoamide, a phosphoneamide or a carboxylic acid amide, preferably a monophosphate. After coupling reaction the nucleosides and the nucleoside analogue are bound preferably by a phosphodiester.

In a preferred embodiment of the invention the artificial nucleobase is a fluorescent DNA intercalator, preferably a cyanine dye, an acridine dye, an ethidium dye, a proflavine dye, a daunomycine dye, an ellipticine dye, an anthracene dye, an quinacrine dye or 5'-, 6'-, 7'- or 8'-hydroxyquinoline. In a more preferred embodiment the artificial nucleobase is thiazole orange (TO).

In a preferred embodiment the probe according to the invention is defined by the general formula 5'-(N1)$_n$—X$_{t1}$-NA-X$_{t2}$-(N2)$_m$—X$_{t3}$-[NA-X$_{t4}$-(N3)$_o$]$_p$-3', wherein N1, N2, N3, NA, X and t1, t2, t3 and t4 are as defined above and
n is an integer from 0 to 20,
m is an integer from 0 to 20,
o is an integer from 0 to 20, and
p is an integer from 0 to 5.

In a more preferred embodiment the probe according to the invention is defined by the general formula 5'-(N1)$_n$—X$_{t1}$-NA-X$_{t2}$-(N2)$_m$—X$_{t3}$-[NA-X$_{t4}$-(N3)$_o$]$_p$-3', wherein
NA is (L)-Serinol(TO), (D)-Serinol(TO), α-(D)-6'-C-deoxyribose(TO) or β-(D)-6'-C-deoxyribose(TO)
n is an integer from 0 to 20
m is an integer from 0 to 15 and
p is 0 and
X is a monophosphate and
t1, t2, t3, t4 is 1.

In a preferred embodiment of the invention the nucleoside analogue is (L)-Serinol(TO), (D)-Serinol(TO), (L)-Threoninol(TO), (D)-Threoninol(TO), (L)-allo-Threoninol(TO), (D)-allo-Threoninol(TO), (L)-iso-Threoninol(TO), (D)-iso-Threoninol(TO), (L)-iso-allo-Threoninol(TO), (D)-iso-allo-Threoninol(TO), α-(D)-6'-C-Deoxyribose(TO) or β-(D)-6'-C-Deoxyribose(TO). The chemical structure is shown in FIG. 3, wherein $R_6$ is a protective group. Every protective group known to the skilled person can be used as $R_6$ according to the present invention. The most preferred protective group is DMTr.

The probes according to the invention show a different fluorescence than DNA based fluorescent hybridization probes of the state of the art. Fluorescence intensity of the single stranded probe is very low and increases significantly after hybridisation to the fully complementary DNA. However, if the probe-target complex comprises a single mismatch adjacent to the fluorescent dye, the fluorescence intensity increases only moderately so that a positive signal is achieved for perfect matched probe-target complexes. Thereby the sensitivity of the fluorescent dye with respect to the direct environment represents a further increase in sensitivity. Thus, the probes according to the present invention can be also used under non-stringent hybridization conditions.

The present invention further relates to the method for production of the nucleoside analogues of the present invention. As building blocks for automated probe synthesis the nucleoside analogues can be chemically synthesized. The synthesis of the ANAAs of the invention is commenced from the DMTr-protected amino alcohols, which were obtained from the corresponding unprotected amino acids. However, the standard procedure for the reaction of the OH-group failed surprisingly so that coupling of the carboxymethylated artificial nucleobase with the DMTr-protected amino alcohol was achieved by converting the primary alcohols into the silyl ethers, by using TBDMSCl. The subsequent coupling of the silyl ethers with the carboxymethylated artificial nucleobase proceeded smoothly when PyBOP was used as activation agent. The TBDMS- and DMTr-protected amino alcohols-fluorescent dye-monomers were desilylated to obtain the desired building blocks of ANAAs for automated probe synthesis.

The synthesis of the carba-sugar building blocks was commenced from the 5',3'-dibenzyl-carba-sugar, which was obtained from cyclopentadiene. Prior to introduction of the dye, the 1'-OH-group was converted to the mesylate. Treatment with the dye and/or precursors thereof (preferably 10-fold excess) under heating over a longer period, especially 20-50 h, yielded the corresponding salt. The diastereomeric mixture was treated with $BBr_3$ to cleave the benzyl ethers. In the next step introduction of the DMTr protective group was needed at the 5'-OH-position. However, the compounds were hardly soluble in pyridine, DMF and acetonitrile. Surprisingly it was found that an exchange of the counter ion solved the solubility problem. $KPF_6$ was added so that after exchange of the counter ion the compounds became soluble in pyridine, DMF and acetonitrile. Under these conditions the DMTr-protection succeeded in 75% yield. The introduction of the DMTr-group also facilitated chromatographic separation of the two diastereomeric carba-sugars.

Detailed synthesis for the different nucleoside analogues is given in the examples.

The present invention further relates to the nucleoside analogues themselves, preferably the present invention relates to (L)-Serinol(TO), (D)-Serinol(TO), (L)-Threoninol(TO), (D)-Threoninol(TO), (L)-allo-Threoninol(TO), (D)-allo-Threoninol(TO), (L)-iso-Threoninol(TO), (D)-iso-Threoninol(TO), (L)-iso-allo-Threoninol(TO), (D)-iso-allo-Threoninol(TO), a-(D)-6'-C-Deoxyribose(TO) and/or b-(D)-6'-C-Deoxyribose(TO). According to the invention the nucleoside analogues are included as free nucleosides having a hydroxyl group at 5'- and/or 3'-position, in the protected form having a protective group at 5'- and/or 3'-position, in the activated form having an activation group at 5'- and/or 3'-position and/or in the bound form having the linker group X, preferably a phosphate group, at 5'- and/or 3'-position. Protective groups are known to the skilled person. Activation of the nucleoside depends on the coupling reaction chosen for automated probe synthesis. Suitable activation groups are known by the skilled person. According to the invention activation by a phosphoamidite group is preferred.

The present invention further relates to a method of production of the probes according to the present invention. Preferably the probes are produced by solid phase synthesis, preferably automated solid phase synthesis. In a more preferred embodiment phosphoamidite-synthesis is used to produce the probes according to the present invention. The general procedure of phosphoamidite synthesis is known by the skilled person.

The present invention further relates to the use of the probes according to the present invention for nucleic acid assays, preferably for homogeneous nucleic acid assays, PCR-reactions, preferably quantitative PCR-reaction, fluorescence in situ hybridization (FISH) assays, in-vitro antisense or antigene assays or traceably knock-out or interference DNA and/or RNA assays. In a preferred embodiment the probes are also used in multiplex assays. Thereby several single base alterations can be detected in one target using one or several probes each having different fluorescent artificial bases. Alternatively one or more single base alterations can be detected in several targets using several probes according to the present invention, wherein for each single base alteration another fluorescent artificial nucleobase is used. Preferably the probes of the present invention are used for in-vitro experiments. However, if artificial nucleobases are used which are therapeutically acceptable, the probes according to the present invention can be used also in in-vivo applications.

The present invention further relates to a kit comprising the components needed for one of the assays disclosed above. The kit comprises at least one or several probes of the present invention and preferably buffer solutions and/or application solutions. Optionally means to perform said assays are also provided by the kit and a written description to perform the assays according to the present invention can be comprised as well.

DETAILED DESCRIPTION OF THE INVENTION

The present invention will be described further in terms of examples which are not intended to limit the invention in any case.

EXAMPLE 1

Synthesis of (D)- and (L)-serinol(TO) (2D and 2L)

Figure 4:
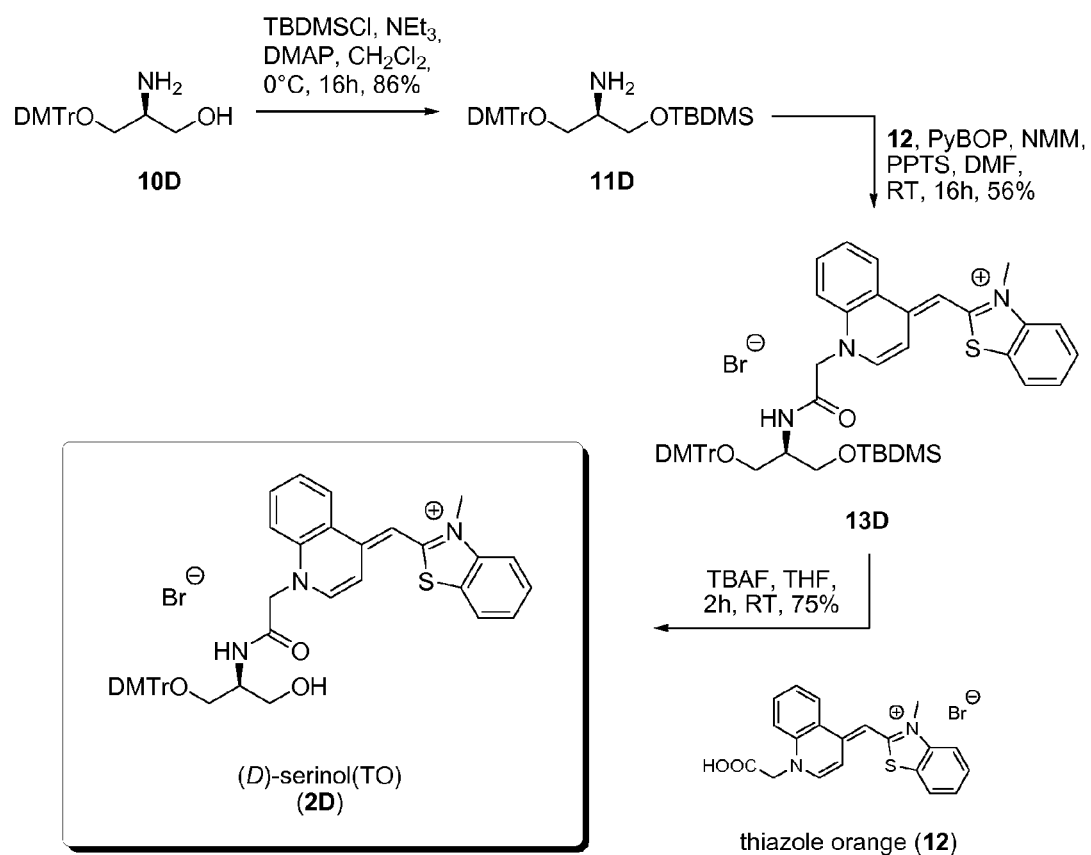
FIG. 4 shows the synthesis of (D)-Serinol(TO) by chemical structures

To obtain the probes according to the present invention the NA building blocks have to be synthesized. Synthesis is shown schematically for (D)-serinol(TO) in FIG. 4.

The synthesis of (D)- and (L)-serinol(TO) (2D and 2L) was commenced from DMTr-protected (D)- and (L)-serinol (10D and 10L), which were obtained from (D)- and (L)-serine, respectively, by following procedures described from R. Benhida et al. [R. Benhida, M. Devis, J. L. Fourrey, F. Lecubin, J. S. Sun, Tetrahedron Letters 1998, 39, 6167]. Standard procedure for reaction of the OH-group failed surprisingly. However, coupling of the carboxymethylated nucleobase (here: thiazole orange, 12) with 10D or 10L was achieved by converting the primary alcohols in 10D and 10L into the silyl ethers 11D and 11L, respectively, by using TBDMSCl. Details of the reaction are given in example 2. The subsequent coupling of 11D and 11L with thiazole orange (12) proceeded smoothly when PyBOP was used as activation agent. The coupling reaction is described in example 3 in detail. The TBDMS- and DMTr-protected serinol(TO)-monomers (13D and 13L) were desilylated to obtain the desired building blocks (D)- and (L)-serinol(TO) (2D and 2L). The desilylation is disclosed in example 4.

EXAMPLE 2

Synthesis of (R)-1-DMTr-3-TBDMS-Serinol (11D) and (S)-1-DMTr-3-TBDMS-Serinol (11L)

(R)-1-DMTr-3-TBDMS-Serinol (11D) was synthesized by adding to a solution of (S)-3-DMTr-serinol (10D) (2.64 g, 6.71 mmol) in 50 mL $CH_2Cl_2$ at 0° C. triethylamine (781 mg, 1.08 mL, 7.72 mmol), dimethylaminopyridine (94.3 mg, 0.772 mmol) and tert-butyldimethylsilyl chloride (1.11 g, 7.38 mmol). After 16 h the reaction mixture was washed with 50 mL saturated aqueous $NaHCO_3$ solution, 2 times with 50 mL water and once with 50 mL saturated aqueous NaCl solution. The organic phase was dried over $MgSO_4$. The solids were removed by filtration and the volatiles removed under reduced pressure. The residue was further purified by flash column chromatography. Yield: 2.92 g (5.75 mmol, 86%), colourless syrup, $C_{30}H_{41}NO_4Si$ (507.74 g/mol). $R_f$=0.75 ($CH_2Cl_2$/MeOH/$NEt_3$, 100:10:0.1, v/v/v). $^1$H-NMR ($CDCl_3$): δ=0.05 (6H, m, $SiMe_2$), 0.89 (9H, s, $Si^tBu$), 3.06 (2H, m, CH, $CH_2$), 3.17 (1H, m, $CH_2$), 3.59 (1H, dd, $J_1$=5.2 Hz, $J_2$=9.8 Hz, $CH_2$), 3.68 (1H, dd, $J_1$=4.4 Hz, $J_2$=9.9 Hz, $CH_2$), 3.80 (6H, s, DMTr-$OCH_3$), 6.85 (4H, m, DMTr), 7.20-7.38 (7H, m, DMTr), 7.48 (4H, m, DMTr). $^{13}$C-NMR ($CDCl_3$): δ=−5.5 ($SiMe_2$), 18.1 ($Si^tBu$), 25.8 ($Si^tBu$), 53.1 (CH), 55.1 (DMTr-$OCH_3$), 65.2 ($CH_2$), 65.2 ($CH_2$), 85.7 (DMTr-$C_q$), 112.9 (4DMTr-ArCH), 126.6 (1DMTr-ArCH), 127.7 (2DMTr-ArCH), 128.1 (2DMTr-ArCH), 130.0 (4DMTr-ArCH), 136.2 (2DMTr-Ar$C_q$), 145.1 (DMTr-Ar$C_q$), 158.3 (2DMTr-Ar$C_q$).

(S)-1-DMTr-3-TBDMS-Serinol (11L) was synthesized by adding to a solution of (R)-3-DMTr-serinol (10L) (2.64 g, 6.71 mmol) in 50 mL $CH_2Cl_2$ at 0° C. triethylamine (781 mg, 1.08 mL, 7.72 mmol), dimethylaminopyridine (94.3 mg, 0.772 mmol) and tert-butyldimethylsilyl chloride (1.11 g, 7.38 mmol). After 16 h the mixture was washed with 50 mL saturated aqueous $NaHCO_3$ solution, 2 times with 50 mL water and once with 50 mL saturated aqueous NaCl solution. The organic phase was dried over $MgSO_4$. The solid material was removed by filtration and the volatiles were removed under reduced pressure. The residue was further purified by flash column chromatography. Yield: 2.11 g (4.16 mmol, 43% d. Th.), colourless syrup, $C_{30}H_{41}NO_4Si$ (507.74 g/mol). $R_f$=0.75 ($CH_2Cl_2$/MeOH/$NEt_3$, 100:10:0.1, v/v/v). $^1$H-NMR ($CDCl_3$): δ=0.05 (6H, m, $SiMe_2$), 0.88 (9H, s, $Si^tBu$), 3.06 (2H, m, CH, $CH_2$), 3.17 (1H, m, $CH_2$), 3.57 (1H, dd, $J_1$=5.2 Hz, $J_2$=9.8 Hz, $CH_2$), 3.68 (1H, dd, $J_1$=4.4 Hz, $J_2$=9.9 Hz, $CH_2$), 3.81 (6H, s, DMTr-$OCH_3$), 6.85 (4H, m, DMTr), 7.20-7.37 (7H, m, DMTr), 7.47 (4H, m, DMTr). $^{13}$C-NMR ($CDCl_3$): δ=−5.5 ($SiMe_2$), 18.2 ($Si^tBu$), 25.8 ($Si^tBu$), 53.1 (CH), 55.1 (DMTr-$OCH_3$), 65.3 ($CH_2$), 65.3 ($CH_2$), 85.7 (DMTr-$C_q$), 113.0 (4DMTr-ArCH), 126.6 (1DMTr-ArCH), 127.7 (2DMTr-ArCH), 128.1 (2DMTr-ArCH), 130.0 (4DMTr-ArCH), 136.2 (2DMTr-Ar$C_q$), 145.1 (DMTr-Ar$C_q$), 158.3 (2DMTr-Ar$C_q$).

EXAMPLE 3

Synthesis of (R)-1-DMTr-3-TBDMS-Serinol(TO) (13D) and (5)-1-DMTr-3-TBDMS-Serinol(TO) (13L)

(R)-1-DMTr-3-TBDMS-Serinol(TO) (13D) was synthesized as shown below. In a volume of 30 mL DMF thiazole orange (12) (1.30 g, 3.02 mmol) was suspended by applying ultra sound over a period of 2 min. Subsequently, PyBOP (1.56 g, 3.02 mmol) and N-methylmorpholine (305 mg, 332 µL, 101.15 mmol) were added. The mixture was stirred for 2 min, whereupon the red suspension considerably cleared up. Subsequently, PPTS (759 mg, 3.02 mmol) was added. The mixture was again stirred for 2 min. To the clear solution was added 1.02 g (2.01 mmol) (R)-1-DMTr-3-TBDMS-Serinol (11D) in 10 mL DMF. The mixture was stirred for 16 h. The volatiles were removed under reduced pressure. The residue was suspended in 100 mL $CH_2Cl_2$. After filtration, the residue was discarded and the filtrate was washed with 100 mL saturated aqueous $NaHCO_3$ solution, twice with mit 100 mL water and dried over $MgSO_4$. The solids were removed by filtration and the volatiles were removed under reduced pressure. The residue was further purified by flash column chromatography. Yield: 1.03 g (1.13 mmol, 56%), red solid, $C_{50}H_{56}BrN_3O_5SSi$ (919.05 g/mol). HRMS (m/z) calculated: 838.3704 $[C_{50}H_{56}N_3O_5SSi]^+$. found: 838.3697. $^1$H-NMR ($CD_3CN$): δ=0.01 (3H, s, $SiMe_2$), 0.02 (3H, s, $SiMe_2$) 0.83 (9H, s, $Si^tBu$), 3.10 (1H, dd, $J_1$=5.4 Hz, $J_2$=9.1 Hz, CHH'), 3.21 (1H, dd, $J_1$=5.7 Hz, $J_2$=9.0 Hz, CHH'), 3.62 (3H, s, TO-$CH_3$), 3.73 (8H, m, 2DMTr-$OCH_3$, $CH_2$), 4.10 (1H, m, CH), 4.90 (2H, s, TO-$CH_2$), 6.33 (1H, s, TO-CH), 6.83 (4H, m, 4DMTr), 6.89 (1H, m, TO), 7.03 (1H, m, TO), 7.10-7.50 (14H, m, 9DMTr, 5TO), 7.57 (1H, m, TO), 7.86 (1H, m, TO), 8.17 (1H, m, TO). $^{13}$C-NMR ($CD_3CN$): δ=−5.3 ($SiMe_2$), −5.3 ($SiMe_2$), 18.7 ($Si^tBu$), 26.1 ($Si^tBu$), 34.6 (TO-$CH_3$), 52.6 (CH), 55.8 (DMTr-$OCH_3$), 57.2 (TO-$CH_2$), 62.7 (2$CH_2$), 86.8 (DMTr-$C_q$), 89.5 (TO-CH), 108.5 (TO—Ar—CH), 113.7 (TO—Ar—CH), 113.9 (4DMTr-ArCH), 118.0 (TO—Ar—CH), 123.3 (TO—Ar—CH), 124.7 (TO—Ar—CH), 125.3 (TO—Ar—$C_q$), 125.7 (TO—Ar—$C_q$), 126.0 (TO—Ar—CH), 127.5 (TO—Ar—CH), 127.7 (1DMTr-ArCH), 128.7 (2DMTr-ArCH), 128.9 (2DMTr-ArCH), 129.1 (TO—Ar—CH), 130.9 (2DMTr-ArCH), 130.9 (2DMTr-ArCH), 134.0 (TO—Ar—CH), 136.8 (DMTr-Ar$C_q$), 137.0 (DMTr-Ar$C_q$), 138.6 (TO—Ar—$C_q$), 141.0 (TO—Ar—$C_q$), 145.5 (TO—Ar—CH), 146.1 (DMTr-Ar—$C_q$), 149.6 (TO—Ar—$C_q$), 159.5 (2DMTr-Ar$C_q$), 161.9 (TO—Ar—$C_q$), 166.1 (TO—$C_q$).

(S)-1-DMTr-3-TBDMS-Serinol(TO) (13L) was synthesized as shown below. In a volume of 30 mL DMF 1.30 g (3.02 mmol) thiazole orange (12) was suspended by applying ultra sound over a period of 2 min. Subsequently, PyBOP (1.56 g, 3.02 mmol) and N-methylmorpholine (305 mg, 332 µL, 101.15 mmol) were added. The mixture was stirred for 2 min, whereupon the red suspension considerably cleared up. PPTS (759 mg, 3.02 mmol) was added. The mixture was stirred for 2 min. To the clear solution was added a solution of 1.02 g (2.01 mmol) (S)-1-DMTr-3-TBDMS-Serinol (11θ in 10 mL DMF. The mixture was stirred for 16 h. The volatiles were removed under reduced pressure. The residue was suspended in 100 mL $CH_2Cl_2$. After filtration the residue was discarded and the filtrate was washed with 100 mL saturated aqueous $NaHCO_3$ solution, twice with mit 100 mL water, dried over $MgSO_4$. After filtration the volatiles were removed under reduced pressure. The residue was further purified by flash column chromatography. Yield: 1.22 g (1.33 mmol, 66% d. Th.), red solid, $C_{50}H_{56}BrN_3O_5SSi$ (919.05 g/mol). HRMS (m/z) calculated: 838.3704 $[C_{50}H_{56}N_3O_5SSi]^+$. found: 838.3705. $^1$H-NMR ($CD_3CN$): δ=−0.00 (3H, s, $SiMe_2$), −0.00 (3H, s, $SiMe_2$) 0.81 (9H, s, $Si^tBu$), 3.11 (1H, dd, $J_1$=5.9 Hz, $J_2$=9.1 Hz, CHH'), 3.21 (1H, dd, $J_1$=5.3 Hz, $J_2$=9.1 Hz, CHH'), 3.66-3.77 (11H, m, $TO\text{-}CH_3$, $2DMTr\text{-}OCH_3$, $CH_2$), 4.08 (1H, m, CH), 5.06 (2H, s, $TO\text{-}CH_2$), 6.51 (1H, s, TO-CH), 6.81 (4H, m, 4DMTr), 7.04 (1H, m, TO), 7.20-7.30 (8H, m, 7DMTr, TO), 7.38-7.55 (7H, m, 2DMTr, 5TO), 7.70 (1H, m, TO), 7.99 (1H, m, TO), 8.31 (1H, m, TO). $^{13}$C-NMR ($CD_3CN$): δ=−5.3 ($SiMe_2$), −5.2 ($SiMe_2$), 18.7 ($Si^tBu$), 26.2 ($Si^tBu$), 34.4 ($TO\text{-}CH_3$), 52.5 (CH), 55.8 ($DMTr\text{-}OCH_3$), 57.1 ($TO\text{-}CH_2$), 62.6 ($CH_2$), 62.7 ($CH_2$), 86.8 ($DMTr\text{-}C_q$), 89.3 (TO-CH), 108.3 (TO—Ar—CH), 113.6 (TO—Ar—CH), 113.9 (4DMTr-ArCH), 117.6 (TO—Ar—CH), 123.2 (TO—Ar—CH), 124.5 (TO—Ar—CH), 125.2 (TO—Ar—$C_q$), 125.6 (TO—Ar—CH), 125.8 (TO—Ar—CH), 127.5 (TO—Ar—CH), 127.7 (1DMTr-ArCH), 128.8 (2DMTr-ArCH), 128.8 (2DMTr-ArCH), 129.1 (TO—Ar—CH), 130.9 (4DMTr-ArCH), 133.9 (TO—Ar—CH), 136.8 (DMTr-Ar$C_q$), 136.9 (DMTr-Ar$C_q$), 138.4 (TO—Ar—$C_q$), 140.9 (TO-Ar—$C_q$), 145.3 (TO—Ar—CH), 146.0 (DMTr-Ar—$C_q$), 149.2 (TO—Ar—$C_q$), 158.3 (2DMTr-Ar$C_q$), 161.5 (TO—Ar—$C_q$), 166.0 (TO—$C_q$).

EXAMPLE 4

Synthesis of (S)-1-DMTr-Serinol(TO) (2D) and (R)-1-DMTr-Serinol(TO) (2L)

Figure 1:
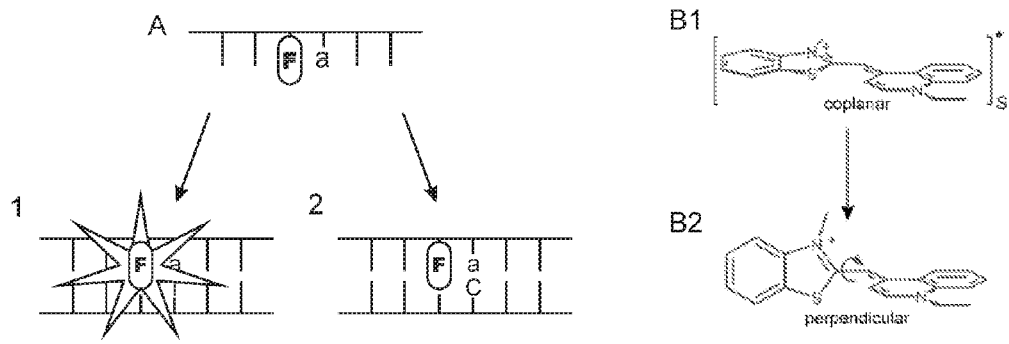
FIG. 1A shows the fluorescence enhancement of the probe according to the invention after perfect match hybridization (FIG. 1A1) compared to mismatch hybridization (FIG. 1A2)
FIG. 1B shows the artificial nucleobase thiazole orange before intercalation into the DNA (FIG. B1) and after intercalation into the DNA (FIG. B2)
Figure 2:
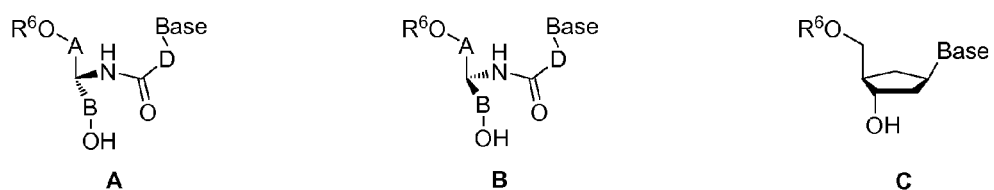
FIG. 2A, B show the chemical structure of the nucleoside analogue having an AANA as modified sugar moiety in D- and L-configuration, respectively
FIG. 2C shows the chemical structure of the nucleoside analogue having β-(D)-6'-C-Deoxyribose as modified sugar moiety
Figure 3:
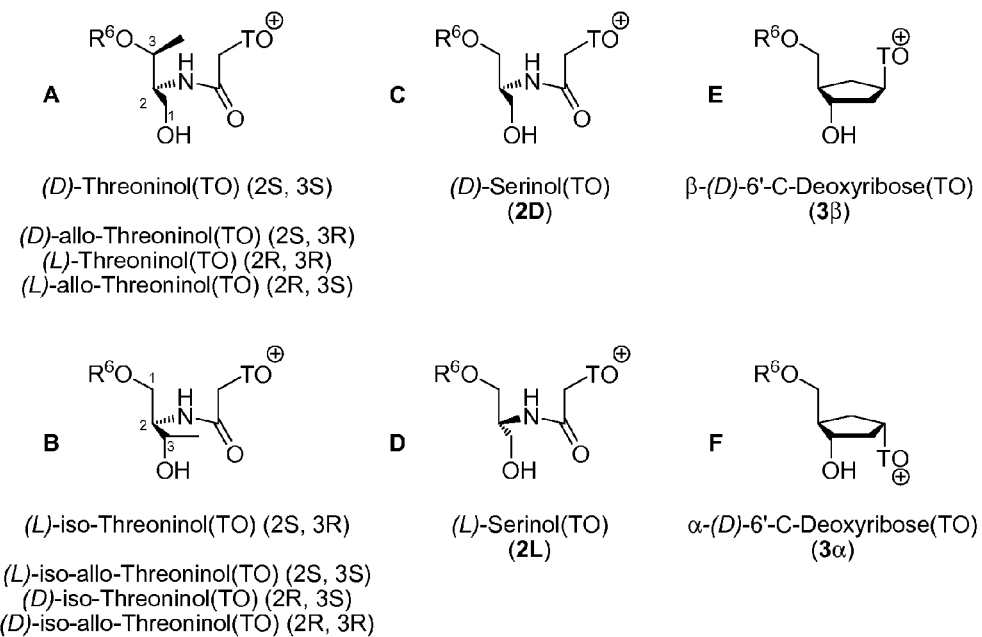
FIG. 3 shows the chemical structure of the preferred nucleoside analogue (L)-/(D)-Threoninol(TO), (L)-/(D)-allo-Threoninol(TO) (FIG. 3 A), (L)-/(D)-iso-Threoninol(TO), (L)-/(D)-iso-allo-Threoninol(TO) (FIG. 3 B), (L)-/(D)-Serinol(TO) (FIG. 3C/D), β-/α-(D)-6'-C-Deoxyribose(TO) (FIG. 3E/F), respectively

(S)-1-DMTr-Serinol(TO) (2D) was synthesized by adding 1.74 mL of a 1M solution of TBAF in THF (1.74 mmol) to a solution of 800 mg (0.872 mmol) (R)-1-DMTr-3-TBDMS-Serinol(TO) (13D) in 15 mL THF under an argon atmosphere. After 1 h 80 mL saturated aqueous $NaHCO_3$ solution was added. The resulting red precipitate was collected, washed 4 times with ethylacetate and dried under reduced pressure. FIG. 3 C shows the chemical structure. Yield: 533 g (0.663 mmol, 76%), red solid, $C_{44}H_{42}BrN_3O_5S$ (804.79 g/mol). HRMS (m/z) calculated: 724.2840 $[C_{44}H_{42}N_3O_5S]^+$. found: 724.2842. $^1$H-NMR ($CD_3CN$): δ=3.11 (2H, m, $CH_2$), 3.63 (3H, s, $TO\text{-}CH_3$), 3.69 (6H, m, $2DMTr\text{-}OCH_3$), 3.77 (1H, m, CHH'), 3.77 (1H, m, CHH'), 4.11 (1H, m, CH), 5.03 (1H, s, J=16.8 Hz, TO-CHH'), 5.21 (1H, s, J=16.7 Hz, TO-CHH'), 6.32 (1H, s, TO-CH), 6.77 (4H, m, 4DMTr), 6.87 (1H, m, TO), 7.10-7.32 (8H, m, 7DMTr, 1TO), 7.36-7.47 (5H, m, 2DMTr, 3TO), 7.55 (1H, m, TO), 7.61 (1H, m, TO), 7.90 (1H, m, TO), 8.08 (1H, m, TO), 8.20 (1H, m, TO). $^{13}$C-NMR ($CD_3CN$): δ=34.5 ($TO\text{-}CH_3$), 53.2 (CH), 55.8 ($2DMTr\text{-}OCH_3$), 57.4 ($TO\text{-}CH_2$), 62.3 ($CH_2$), 63.2 ($CH_2$), 86.7 (DMTr-$C_q$), 89.2 (TO-CH), 108.5 (TO—Ar—CH), 113.5 (TO—Ar—CH), 113.9 (4DMTr-ArCH), 123.4 (TO—Ar—CH), 124.6 (TO—Ar—$C_q$), 125.2 (TO—Ar—$C_q$), 125.6 (TO—Ar—CH), 125.8 (TO—Ar—CH), 127.5 (TO—Ar—CH), 127.7 (1DMTr-ArCH), 128.7 (2DMTr-ArCH), 128.9 (2DMTr-ArCH), 129.1 (TO—Ar—CH), 130.9 (4DMTr-ArCH), 134.0 (TO—Ar—CH), 136.9 (DMTr-Ar$C_q$), 136.9 (DMTr-Ar$C_q$), 138.6 (TO—Ar—$C_q$), 141.1 (TO—Ar—$C_q$), 145.6 (TO—Ar—CH), 146.0 (DMTr-Ar—$C_q$), 149.3 (TO—Ar—$C_q$), 159.5 (2DMTr-Ar$C_q$), 161.4 (TO—Ar—$C_q$), 166.5 (TO—$C_q$).

(R)-1-DMTr-Serinol(TO) (2L) was synthesized by adding 600 µL of a 1M solution of TBAF in THF (0.600 mmol) to a solution of 276 mg (0.300 mmol) (S)-1-DMTr-3-TBDMS-Serinol(TO) (13L) in 5 mL THF under an argon atmosphere. After 1 h 50 mL saturated aqueous $NaHCO_3$ solution were added. The resulting red precipitate was collected, washed 4 times with ethylacetate and dried under reduced pressure. FIG. 3 D shows the chemical structure. Yield: 181 g (0.225 mmol, 75%), red solid, $C_{44}H_{42}BrN_3O_5S$ (804.79 g/mol). HRMS (m/z) calculated: 724.2840 $[C_{44}H_{42}N_3O_6S]^+$. found: 724.2847. $^1$H-NMR ($CD_3CN$): δ=3.11 (2H, m, $CH_2$), 3.63 (3H, s, $TO\text{-}CH_3$), 3.69 (6H, m, $2DMTr\text{-}OCH_3$), 3.77 (1H, m, CHH'), 3.77 (1H, m, CHH'), 4.11 (1H, m, CH), 5.03 (1H, s, J=16.8 Hz, TO-CHH'), 5.21 (1H, s, J=16.7 Hz, TO-CHH'), 6.32 (1H, s, TO-CH), 6.77 (4H, m, 4DMTr), 6.87 (1H, m, TO), 7.10-7.32 (8H, m, 7DMTr, 1TO), 7.36-7.47 (5H, m, 2DMTr, 3TO), 7.55 (1H, m, TO), 7.61 (1H, m, TO), 7.90 (1H, m, TO), 8.08 (1H, m, TO), 8.20 (1H, m, TO). $^{13}$C-NMR ($CD_3CN$): δ=34.5 ($TO\text{-}CH_3$), 53.2 (CH), 55.8 ($2DMTr\text{-}OCH_3$), 57.4 ($TO\text{-}CH_2$), 62.3 ($CH_2$), 63.2 ($CH_2$), 86.7 (DMTr-$C_q$), 89.2 (TO-CH), 108.5 (TO—Ar—CH), 113.5 (TO—Ar—CH), 113.9 (4DMTr-ArCH), 123.4 (TO—Ar—CH), 124.6 (TO—Ar—$C_q$), 125.2 (TO—Ar—$C_q$), 125.6 (TO—Ar—CH), 125.8 (TO—Ar—CH), 127.5 (TO—Ar—CH), 127.7 (1DMTr-ArCH), 128.7 (2DMTr-ArCH), 128.9 (2DMTr-ArCH), 129.1 (TO—Ar—CH), 130.9 (4DMTr-ArCH), 134.0 (TO—Ar—CH), 136.9 (DMTr-Ar$C_q$), 136.9 (DMTr-Ar$C_q$), 138.6 (TO—Ar—$C_q$), 141.1 (TO—Ar—$C_q$), 145.6 (TO—Ar—CH), 146.0 (DMTr-Ar—$C_q$), 149.3 (TO—Ar—$C_q$), 159.5 (2DMTr-Ar$C_q$), 161.4 (TO—Ar—$C_q$), 166.5 (TO—$C_q$).

EXAMPLE 5

Synthesis of α- and β-(D)-Carba-2'-desoxyribose (TO) (3α and 3β)

Figure 5:
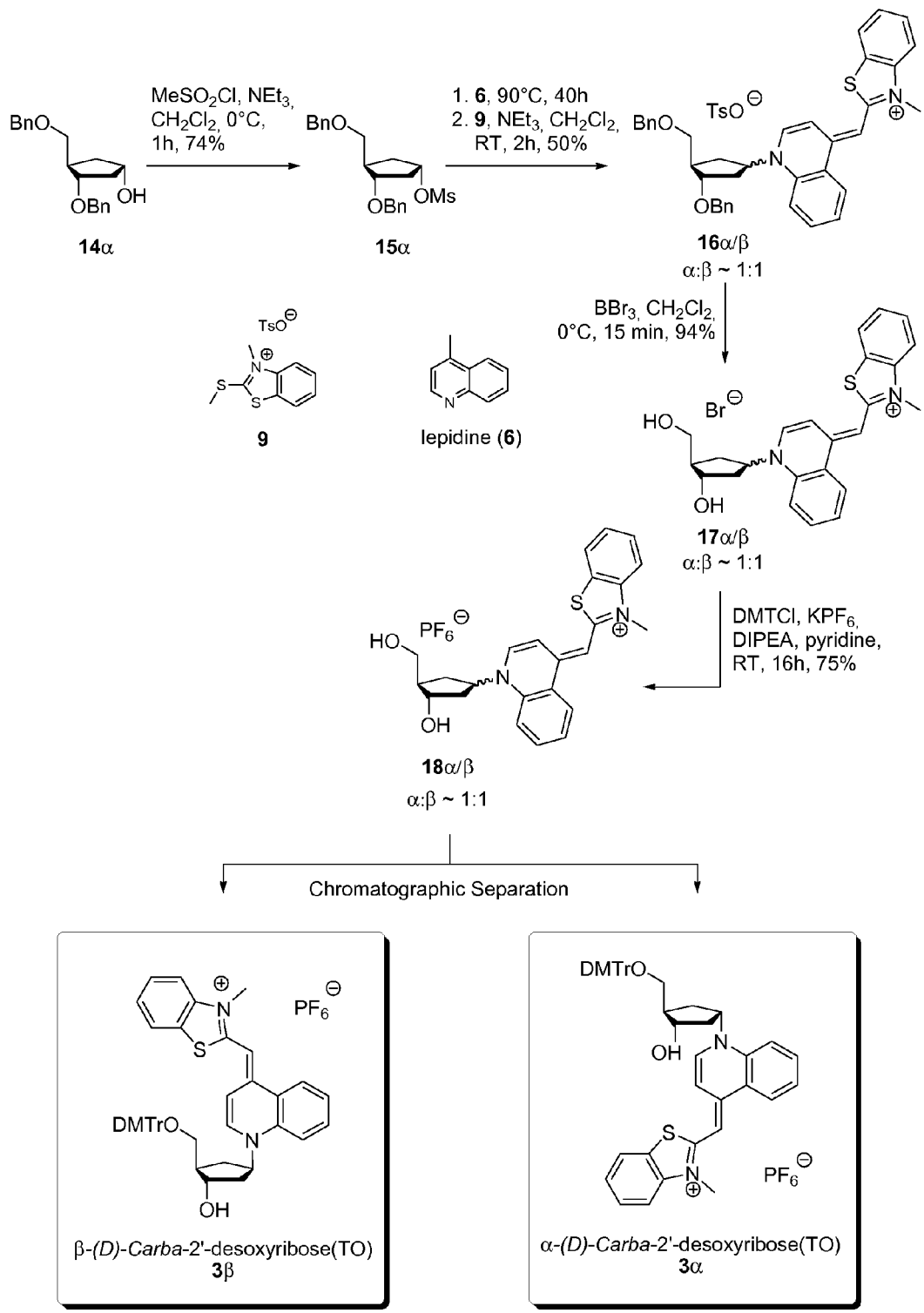
FIG. 5 shows the synthesis of β-/α-(D)-Carba-2'-deoxyribose(TO) by chemical structures

The synthesis of the α- and β-(D)-Carba-2'-desoxyribose (TO) (3α and 3β) building blocks was commenced from α-(D)-5',3'-dibenzyl-carba-2'-desoxyribose (14α), which was obtained from cyclopentadiene as disclosed by O. R. Ludek, et al. [O. R. Ludek, C. Meier, Synthesis-Stuttgart 2003, 2101]. Prior to introduction of lepidine (6), the 1'-OH-group was converted to the mesylate in 15α (Example 6). Treatment of 15α with neat lepidine (10-fold excess) at 90° C. over a period of 40 h yielded the lepidinium salt 16α/β (Example 7). The diastereomeric mixture 16α/β was treated with $BBr_3$ to cleave the benzyl ethers (Example 8). In the next step introduction of the DMTr protective group was needed at the 5'-OH-position. However, 17α/β in pyridine was hardly soluble in DMF and acetonitrile. Surprisingly it was found that an exchange of the counter ion in 17α/β solved the solubility problem. $KPF_6$ was added so that after exchange of the counter ion 18α/β was achieved being soluble in DMF and acetonitrile. Under these conditions the DMTr-protection succeeded in 75% yield of 3α/β (Example 9). The introduction of the DMTr-group also facilitated chromatographic separation of the two diastereomers 3α and 3β. Scheme FIG. 5 shows the synthesis procedure in detail.

EXAMPLE 6

Synthesis of α-(D)-5',2'-Dibenzyl-carba-2'-desoxyribosyl-1'-methylsulfonat (15α)

To a solution of 3.37 g (10.8 mmol) α-(D)-5',2'-Dibenzyl-carba-2'-desoxyribose (14α) in 200 mL dry $CH_2Cl_2$ at 0° C.

was added under an argon atmosphere 8.73 g (86.3 mmol, 12.1 mL) triethylamine. Subsequently, a solution of 9.89 g (86.3 mmol, 6.72 mL) methanesulfonic acid chloride in 20 mL $CH_2Cl_2$ was added drop wise over a period of 1 h. After one hour 100 mL saturated aqueous $NaHCO_3$ solution was added and the organic phase was separated. The aqueous layer was twice extracted with 100 mL $Et_2O$. The combined organic phases were dried over $MgSO_4$, filtered and concentrated at reduced pressure. The residue was further purified by flash column chromatography. Yield: 3.94 g (10.1 mmol, 93%), colourless oil, $O_{21}H_{26}O_5S$ (390.40 g/mol). $R_f$=0.78 (EtOAc/cyclohexane, 1:1, v/v). $[\alpha]_D^{20}$=30.8° (c=1.00, $CHCl_3$). $^1$H-NMR ($CDCl_3$): δ=1.91 (1H, ddd, $J_1$=6.1, $J_2$=8.6, $J_3$=14.4, H5), 2.13 (1H, m, H2), 2.25 (1H, m, H5'), 2.38 (1H, m, H5'), 2.57 (1H, m, H4), 2.98 (3H, s, $CH_3SO_2$—), 3.47 (2H, m, H6, H6'), 3.90 (1H, m, H3), 4.51 (4H, m, $2CH_2$), 5.15 (1H, m, H1), 7.27-7.39 (10H, m, 10Ar—CH). $^{13}$-NMR ($CDCl_3$): δ=35.1 (C5), 38.7 ($CH_3$), 39.2 (C2), 44.5 (C4), 70.8 (C6), 71.4 ($CH_2$), 73.1 ($CH_2$), 80.2 (C3), 81.8 (C1), 127.6 (2Ar—CH), 127.7 (Ar—CH), 127.7 (Ar—CH), 127.7 (2Ar—CH), 128.4 (2Ar—CH), 128.4 (2Ar—CH), 138.3 (Ar—$C_q$), 138.4 (Ar—$C_q$).

EXAMPLE 7

Synthesis of α/β-(D)-5',2'-Dibenzyl-carba-2'-desoxyribose(TO) (16α/β)

In a round bottom flask 3.02 g (7.72 mmol) β-(D)-5',2'-dibenzyl-carba-2'-desoxyribosyl-1'-methylsulfonate (15β) and 11.1 g (77.2 mmol) lepidine (6) were heated to 100° C. for 48 h. After cooling to room temperature 150 mL $CH_2Cl_2$ were added, followed by 5.67 g (15.4 mmol) 3-methyl-2-thiomethyl-benzothiazolium tosylate (9) and 3.12 g (30.9 mmol, 4.34 mL) triethylamine. The addition of triethylamine caused an instant colour change to red. After stirring for 4 h under the exclusion of light, the mixture was washed 4 times with 100 mL of a 1M aqueous HCl solution. The organic phase was dried over $MgSO_4$, filtered and concentrated. The residue was further purified using flash column chromatography. Yield: 2.10 g (2.78 mmol, 36%), red solid, $C_{45}H_{44}N_2O_5S_2$ (757.0 g/mol). $R_f$=0.53 ($CH_2Cl_2$/MeOH/$NEt_3$, 90:10:0.1, v/v/v). Ratio of diastereomers: α/β=5:1.

By using the same procedure as mentioned above 3.94 g (10.1 mmol) α-(D)-5',2'-dibenzyl-carba-2'-desoxyribosyl-1'-methylsulfonate (15α) and 14.5 g (100.9 mmol) lepidine (6), as well as 7.42 g (20.18 mmol) 3-methyl-2-thiomethyl-benzothiazolium tosylate (9) and 4.08 g (40.36 mmol, 5.67 mL) triethylamine in 200 mL $CH_2Cl_2$ were allowed to react. Yield: 1.68 g (2.22 mmol, 22%), red solid, $C_{45}H_{44}N_2O_5S_2$ (757.0 g/mol). $R_f$=0.53 ($CH_2Cl_2$/MeOH/$NEt_3$, 90:10:0.1, v/v/v). Ratio of diastereomers: α/β=1:1.

HRMS (m/z) calculated: 585.2570 $[C_{38}H_{37}N_2O_2S]^+$. found: 585.2568. $^1$H-NMR ($CDCl_3$): δ=1.72 (1H, m), 2.10 (2H, m), 2.21 (6H, s, Ts-$CH_3$), 2.31 (2H, m), 2.53 (5H, m), 3.45 (4H, m, 2H5, 2H5'), 3.77 (6H, m $2CH_3$), 3.99 (2H, m, 2H3), 4.44 (8H, m, 4Bn-$CH_2$), 4.94 (1H, m, H1), 5.10 (1H, m, H1), 6.61 (2H, s, 2CH), 7.02-7.62 (40H, m), 7.88 (4H, m, 4Ts—Ar—CH), 8.57 (3H, m, 3TO—Ar—CH), 8.80 (1H, m, 1TO—Ar—CH). $^{13}$C-NMR ($CDCl_3$): δ=21.2 (2Ts-$CH_3$), 34.1 (C6), 34.2 ($2CH_3$), 34.2 (C6), 37.4 (C2), 38.4 (C2), 44.5 (C4), 44.7 (C4), 60.4 (C1), 61.5 (C1), 71.0 ($CH_2$), 71.1 ($CH_2$), 71.5 ($CH_2$), 71.6 ($CH_2$), 73.1 ($CH_2$), 73.2 ($CH_2$), 79.6 (C3), 81.0 (C3), 88.5 (CH), 88.6 (CH), 108.7 (TO—Ar—CH), 109.5 (TO—Ar—CH), 111.8 (2TO—Ar—CH), 115.9 (1TO—Ar—CH), 116.9 (1TO—Ar—CH), 121.9 (1TO—Ar—CH), 122.0 (1TO—Ar—CH), 123.9 (1TO—Ar—CH), 124.0 (1TO—Ar—CH), 124.2 (1TO—Ar—$C_q$), 124.3 (1TO—Ar—$C_q$), 124.5 (2TO—Ar—$C_q$), 126.1 (4Ts-Ar—CH), 126.2 (1TO—Ar—CH), 126.4 (1TO—Ar—CH), 126.6 (1TO—Ar—CH), 126.8 (1TO—Ar—CH), 127.1 (1TO—Ar—CH), 127.5 (2TO—Ar—CH), 127.6 (4Ts-Ar—CH, 4Bn-Ar—CH), 127.6 (4Bn-Ar—CH), 128.1 (TO—Ar—CH), 128.2 (2Bn-CH—Ar), 128.3 (2Bn-CH—Ar), 128.3 (4Bn-CH—Ar), 128.4 (4Bn-CH—Ar), 131.1 (1TO—Ar—CH), 132.5 (1TO—Ar—CH), 137.1 (Bn-Ar—$C_q$), 137.4 (Bn-Ar—$C_q$) 137.9 (Bn-Ar—$C_q$), 138.1 (2TO—Ar—$C_q$), 138.2 (Bn-Ar—$C_q$), 138.6 (2Ts-Ar—CH), 139.9 (1TO—Ar—$C_q$), 140.0 (1TO—Ar—$C_q$), 140.3 (1TO—Ar—CH), 140.4 (1TO—Ar—CH), 139.9 (2TO—Ar—$C_q$), 140.0 (2TO—Ar—$C_q$), 140.4 (1TO—Ar—CH), 140.3 (1TO—Ar—CH), 144.7 (2Ts-ArCH), 148.2 (1TO—Ar—$C_q$), 148.3 (1TO—Ar—$C_q$), 159.5 (1TO—Ar—$C_q$), 159.6 (1TO—Ar—$C_q$).

EXAMPLE 8

Synthesis of α/β-(D)-Carba-2'-desoxyribose(TO) (17α/β)

Under argon, $BBr_3$ (2.61 g, 1.02 mL, 10.4 mmol) was added drop wise to a cooled (0° C.) solution of 1.58 g (2.09 mmol) α/β-(D)-5',2'-dibenzyl-carba-2'-desoxyribose(TO) (16α/β) in 60 mL dry $CH_2Cl_2$. Complete addition resulted in a colourless suspension, to which after 10 min 150 mL saturated aqueous $NaHCO_3$ solution were added. After 30 min the red precipitate was collected, dried under reduced pressure and used without further purification. Yield: quantitatively, red solid, $C_{24}H_{25}BrN_2O_5S$ (485.4 g/mol). HRMS (m/z) calculated: 405.1631 $[C_{24}H_{25}N_2O_2S]^+$. found: 405.1628. $R_f$=0.15 ($CH_2Cl_2$/MeOH/$NEt_3$, 90:10:0.1, v/v/v). Ratio of diastereomers: α/β=as the starting material. $^1$H-NMR (DMSO-$D_6$): δ=1.71 (1H, m), 2.12 (8H, m), 2.58 (1H, m), 3.51 (4H, m, 2H5, 2H5'), 3.97 (6H, s, $2CH_3$), 4.14 (2H, m, 2H3), 5.47 (2H, m, 2H), 6.83 (2H, s, 2CH), 7.33 (4H, m, 4TO—Ar—CH), 7.53 (2H, m, 2TO—Ar—CH), 7.71 (4H, m, 4TO—Ar—CH), 7.97 (4H, m, 4TO—Ar—CH), 8.21 (2H, m, 2TO—Ar—CH), 8.76 (4H, m, 4TO—Ar—CH). $^{13}$C-NMR (DMSO-$D_6$): δ=33.8 ($CH_3$), 33.8 ($CH_3$), 34.0 (2C6), 40.2 (C2), 40.6 (C2), 48.8 (C4), 49.3 (C4), 59.8 (C1), 60.4 (C1), 61.8 (C5), 61.9 (C5), 70.9 (C3), 71.9 (C3), 87.8 (CH), 87.9 (CH), 108.1 (2TO—Ar—CH), 112.8 (1TO—Ar—CH), 114.0 112.8 (1TO—Ar—CH), 117.8 (1TO—Ar—CH), 117.9 (1TO—Ar—CH), 122.7 (1TO—Ar—CH), 122.8 (1TO—Ar—CH), 123.7 (2TO—Ar—$C_q$), 124.1 (1TO—Ar—$C_q$), 124.1 (1TO—Ar—$C_q$), 124.2 (1TO—Ar—CH), 124.3 (1TO—Ar—CH), 125.7 (2TO—Ar—CH), 126.6 (1TO—Ar—CH), 126.6 (1TO—Ar—CH), 128.0 (2TO—Ar—CH), 133.0 (1TO—Ar—CH), 133.1 (1TO—Ar—CH), 137.5 (1TO—Ar—$C_q$), 137.7 (1TO—Ar—$C_q$), 140.1 (1TO—Ar—CH), 140.2 (2TO—Ar—$C_q$), 140.9 (1TO—Ar—CH), 147.9 (1TO—Ar—$C_q$), 147.9 (1TO—Ar—$C_q$), 159.6 (1TO—Ar—$C_q$), 159.7 (1TO—Ar—$C_q$).

EXAMPLE 9

Synthesis of α/β-(D)-5'-DMTr-carba-2'-desoxyribose (TO) (3α/β)

In an argon atmosphere $KPF_6$ (769 mg, 4.18 mmol) was added to a solution of 2.09 mmol α/β-(D)-Carba-2'-desoxyribose(TO) (17α/β) in 100 mL dry pyridine. The turbid solution became clear and 2.70 g (20.9 mmol, 3.45 mL) diisopropylethylamine and 3.40 g (10.0 mmol) DMTrCl were added.

After 16 h the mixture was filtered and the residue was discarded. The filtrate was concentrated under reduced pressure and dichlormethane was added. The organic phase was 3 times washed with saturated aqueous $NaHCO_3$ solution, dried over $MgSO_4$, filtered and concentrated at reduced pressure. The residue was further purified by flash column chromatography, in which the separation of the diastereomers was made. Yield: 1.51 g (1.77 mmol, 85%), red solid, $C_{45}H_{43}F_6N_2O_4PS$ (852.9 g/mol). $R_f$=0.80 ($CH_2Cl_2$/MeOH/ $NEt_3$, 90:10:0.1, v/v/v). Ratio of diastereomers: α/β=as the starting material.

α-(D)-5'-DMTr-carba-2'-desoxyribose(TO) (3α): $[α]_D^{20}$=−32.3° (c=0.10, $CHCl_3$). FIG. 3 F shows the chemical structure. HRMS (m/z) calculated: 707.2938 $[C_{45}H_{43}N_2O_4S]^+$. found: 707.2930. $^1$H-NMR ($CD_3CN$): δ=2.05 (1H, m, H2), 2.19 (2H, m, H6, H6'), 2.39 (1H, m, H4), 2.61 (1H, m, H2'), 3.18 (2H, m, H5, H5'), 3.76 (3H, s, $CH_3$), 3.77 (6H, s, $2CH_3$), 4.28 (1H, m, H3), 5.19 (1H, m, H1), 6.56 (2H, s, CH), 6:89 (4H, m, 4DMTr-Ar—CH), 7.21 (1H, m, 1TO—Ar—CH), 7.27 (2H, m, 1DMTr-Ar—CH, 1TO—Ar—CH), 7.35 (7H, m, 6DMTr-Ar—CH, 1TO—Ar—CH), 7.47 (3H, m, 1TO—Ar—CH, 2DMTr-Ar—CH), 7.61 (1H, m, 1TO—Ar—CH), 7.77 (3H, m, 1TO—Ar—CH), 8.42 (1H, m, 1TO—Ar—CH), 8.57 (1H, m, 1TO—Ar—CH). $^{13}$C-NMR ($CD_3CN$): δ=34.4 ($CH_3$), 35.5 (C6), 41.5 (C2), 48.6 (C4), 55.9 ($2CH_3$), 61.9 (C1), 65.1 (C5), 74.3 (C3), 86.9 (DMTr-$C_q$), 88.6 (CH), 109.3 (1TO—Ar—CH), 113.3 (1TO—Ar—CH), 114.0 (4DMTr-Ar—CH), 118.5 (1TO—Ar—CH), 123.3 (1TO—Ar—CH), 125.1 (1TO—Ar—$C_q$), 125.4 (1TO—Ar—$C_q$), 125.4 (1TO—Ar—CH), 126.2 (1TO—Ar—CH), 127.5 (1TO—Ar—CH), 127.8 (DMTr-Ar—CH), 128.8 (2DMTr-Ar—CH), 129.0 (2DMTr-Ar—CH), 129.0 (1TO—Ar—CH), 131.0 (4DMTr-Ar—CH), 133.9 (1TO—Ar—CH), 137.1 (DMTr-Ar—$C_q$), 137.1 (DMTr-Ar—$C_q$), 138.9 (1TO—Ar—$C_q$), 141.3 (1TO—Ar—$C_q$), 141.4 (1TO—Ar—CH), 146.3 (DMTr-Ar—$C_q$), 149.4 (1TO—Ar—$C_q$), 159.6 (2DMTr-Ar—$C_q$), 161.1 (1TO—Ar—$C_q$).

β-(D)-5'-DMTr-carba-2'-desoxyribose(TO) (3β): $[α]_D^{20}$=40.2° (c=0.10, $CHCl_3$). FIG. 3 E shows the chemical structure. HRMS (m/z) calculated: 707.2938 $[C_{45}H_{43}N_2O_4S]^+$. found: 707.2928. $^1$H-NMR ($CD_3CN$): δ=1.67 (1H, m, H6), 2.26 (3H, m, H2, H2', H4), 2.63 (1H, m, H6'), 3.22 (2H, m, H5, H5'), 3.72 (6H, s, $2CH_3$), 3.81 (3H, s, $CH_3$), 4.32 (1H, m, H3), 5.33 (1H, m, H1), 6.63 (2H, s, CH), 6:84 (4H, m, 4DMTr-Ar—CH), 7.18 (1H, m, 1TO—Ar—CH), 7.23 (1H, m, 1DMTr-Ar—CH), 7.30 (6H, m, 6DMTr-Ar—CH), 7.34 (1H, m, 1TO—Ar—CH), 7.43 (3H, m, 1TO—Ar—CH, 2DMTr-Ar—CH), 7.51 (1H, m, 1TO—Ar—CH), 7.66 (1H, m, 1TO—Ar—CH), 7.78 (1H, m, 1TO—Ar—CH), 7.87 (1H, m, 1TO—Ar—CH), 7.98 (1H, m, 1TO—Ar—CH), 8.27 (1H, m, 1TO—Ar—CH), 8.48 (1H, m, 1TO—Ar—CH). $^{13}$C-NMR ($CD_3CN$): δ=34.5 ($CH_3$), 35.2 (C6), 41.1 (C2), 48.0 (C4), 55.8 ($2CH_3$), 61.0 (C1), 64.5 (C5), 73.0 (C3), 86.9 (DMTr-$C_q$), 88.8 (CH), 109.3 (1TO—Ar—CH), 113.4 (1TO—Ar—CH), 114.0 (2DMTr-Ar—CH), 114.0 (2DMTr-Ar—CH), 118.7 (1TO—Ar—CH), 123.4 (1TO—Ar—CH), 125.1 (1TO—Ar—$C_q$), 125.4 (1TO—Ar—$C_q$), 125.5 (1TO—Ar—CH), 126.2 (1TO—Ar—CH), 127.7 (1TO—Ar—CH), 127.8 (DMTr-Ar—CH), 128.8 (2DMTr-Ar—CH), 129.0 (2DMTr-Ar—CH), 129.1 (1TO—Ar—CH), 130.9 (2DMTr-Ar—CH), 130.9 (2DMTr-Ar—CH), 134.1 (1TO—Ar—CH), 137.1 (DMTr-Ar—$C_q$), 137.2 (DMTr-Ar—$C_q$), 139.0 (1TO—Ar—$C_q$), 140.2 (1TO—Ar—$C_q$), 141.4 (1TO—Ar—$C_q$), 146.1 (DMTr-Ar—$C_q$), 149.5 (1TO—Ar—$C_q$), 159.5 (2DMTr-Ar—$C_q$), 161.3 (1TO—Ar—$C_q$).

EXAMPLE 10

Synthesis of (R)-1-DMTr-Serinol(TO)-3-(O-Cyanoethyl-N,N-di$^i$pr)-phosphoamidite (25D) and (S)-1-DMTr-serinol(TO)-3-(O-Cyanoethyl-N,N-di$^i$pr)-phosphoamidite (25L)

Figure 6:
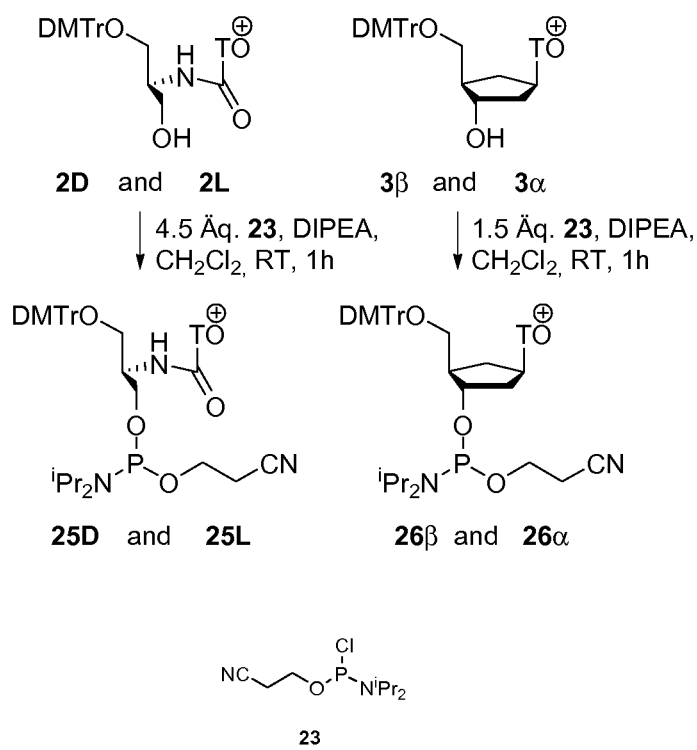
FIG. 6 shows the chemical structure of the activated nucleoside analogues

For phosphoamidite synthesis, the TO-labelled monomers 2D, 2L were treated with chloro(2-cyanoethoxy)(diiso-propylamino)phosphine (23) as shown in FIG. 6. (R)-1-DMTr-Serinol(TO)-3-(O-Cyanoethyl-N,N-di$^i$pr)-phosphoamidite (25D) was synthesized as shown below. In an argon atmosphere 295 mg (0.366 mmol) (S)-Serinol(TO) (2D) was dissolved in 10 mL dry $CH_2Cl_2$ and 283 mg (383 μL, 2.20 mmol) DIPEA was added, followed by 390 mg (1.65 mmol, 368 μL) 2-cyanoethyl-N,N-diisopropyl-chlorophosphorodiamidite (23). After 1 h, the reaction was stopped by the addition of 10 mL saturated aqueous $NaHCO_3$ solution. The organic phase was separated, washed twice with saturated aqueous $NaHCO_3$ solution, dried over $MgSO_4$ and concentrated. The crude product was dissolved in 1.8 mL dry acetonitrile, filtered and used without further purification for automated DNA synthesis. Yield: quantitative, red solid, $C_{53}H_{59}BrN_5O_6PS$ (1005.0 g/mol). $R_f$=0.65 ($CH_2Cl_2$/MeOH/ $NEt_3$, 89.5/10/0.5, v/v/v). $^{31}$P-NMR ($CD_3CN$): δ=148.159, 147.650.

For preparation of (S)-1-DMTr-serinol(TO)-3-(O-Cyanoethyl-N,N-di$^i$pr)-phosphoamidit (25L) a solution of 345 mg (0.427 mmol) (R)-serinol(TO) (2L) in 15 mL dry $CH_2Cl_2$ was allowed to react with 331 mg (447 μL, 2.56 mmol) DIPEA and 454 mg (1.92 mmol, 428 μL) 2-cyanoethyl-N,N-diisoropyl-chlorophosphorodiamidite (23) as described above. The crude product was dissolved in 2.1 mL dry acetonitrile, filtered and used without further purification for automated DNA synthesis. Yield: quantitative, red solid, $C_{53}H_{59}BrN_5O_6PS$ (1005.0 g/mol). $R_f$=0.64 ($CH_2Cl_2$/MeOH/ $NEt_3$, 89.5/10/0.5, v/v/v). $^{31}$P-NMR ($CD_3CN$): δ=148.159, 147.650.

EXAMPLE 11

Synthesis of α-(D)-5'-DMTr-carba-2'-desoxyribose (TO)-3'-(O-cyanoethyl-N,N-d$^i$ipr)-phosphoamidite (26α) and β-(D)-5'-DMTr-carba-2'-desoxyribose (TO)-3'-(O-cyanoethyl-N,N-di$^i$pr)-phosphoamidite (26β)

For phosphoamidite synthesis, the TO-labelled monomers 3α and 3β were treated with chloro(2-cyanoethoxy)(diisopropylamino)phosphine (23) as shown in FIG. 6. α-(D)-5'-DMTr-carba-2'-desoxyribose(TO)-3'-(O-cyanoethyl-N,N-di$^i$pr)-35 phosphoamidite (26α) was synthesized following the procedure of example 10. 640 mg (0.750 mmol) α-(D)-Carba-2'-Desoxyribose(TO) (3α) in 30 mL dry $CH_2Cl_2$, 291 mg (393 μL, 2.25 mmol) DIPEA and 266 mg (1.13 mmol, 251 μL) 2-cyanoethyl-N,N-diisopropyl-chlorophosphorodiamidite (23) were reacted. The crude product was dissolved in 3.7 mL dry acetonitrile, filtered and used without further purification for automated DNA synthesis. Yield: quantitative, red solid, $C_{54}H_{60}F_6N_4O_5P_2S$ (1053.1 g/mol). $R_f$=0.44 ($CH_2Cl_2$/ MeOH/$NEt_3$, 95.5/5/0.5, v/v/v). $^{31}$P-NMR ($CD_3CN$): δ=148.379, 147.870.

For preparation of β-(D)-5'-DMTr-carba-2'-desoxyribose (TO)-3'-(O-cyanoethyl-N,N-di$^i$pr)-phosphoamidite (2613

312 mg (0.366 mmol) β-(D)-Carba-2'-Desoxyribose(TO) (3β) in 40 mL dry $CH_2Cl_2$, 142 mg (192 μL, 1.10 mmol) DIPEA and 133 mg (0.549 mmol, 123 μL) 2-cyanoethyl-N,N-diisopropyl-chlorophosphorodiamidite (23) were reacted as described in example 10. The crude product was dissolved in 1.9 mL dry acetonitrile, filtered and used without further purification for automated DNA synthesis. Yield: quantitative, red solid, $C_{54}H_{60}F_6N_4O_5P_2S$ (1053.1 g/mol). $R_f$=0.38 ($CH_2Cl_2$/MeOH/NEt$_3$, 95.5/5/0.5, v/v/v). $^{31}$P-NMR (CD$_3$CN): δ=147.462, 147.118.

EXAMPLE 12

Synthesis of TO-labelled FIT-DNA-Probes

The phosphoamidites 25D, 25L, 26α and 26β of Examples 10 and 11 were used without further purification. The reactivity of said TO-labelled monomers was equal to commercially available phosphoamidites. Cleavage of the oligomers from the solid support and removal of protective groups was induced with aqueous concentrated ammonia solution (2 h, RT) or with $K_2CO_3$ in methanol (4 h, RT). However, the oligomers can be treated with aqueous concentrated ammonia solution for 4 h at 55° C. without any problems. These conditions are equal to the protocols of liberation and protective group removal if standard dT-, dA$^{Bz}$-, dC$^{BZ}$ and dG$^{DMF}$-nucleosides are used. Hence, the usage of UltraMILD-phosphoamidites is not mandatory. Further purification was achieved by following known DMTr-ON/OFF purification protocols and using semi preparative HPLC. The oligonucleotides were desalted through gel permeation chromatography.

The DNA-FIT-probes were assembled on a ABI 3400-DNA-Synthesizer by using the TO-nucleosid-phosphoamidites and commercially available UltraMILD dT-, dA$^{Pac}$-, dC$^{Ac}$- and dG$^{iPr-Pac}$-nucleosides following manual instruction.

The oligodeoxynucleotides were assembled by using an AB Applied Biosystems Synthesizer Model 3400 and phosphoamidite methodology. CPGs were purchased from Applied Biosystems and Link Technologies (1 μmol, pore size 500 Å) and DNA syntheses reagents from Applied Biosystems and Roth (dry acetonitrile, 2% dichloroacetic acid in $CH_2Cl_2$, 4% tetrazole in acetonitrile, acetic anhydrid in 2,6-Lutidine/THF (1/1/8), 16% 1-methylimidazole in THF, Iod in water/pyridine/THF (3/2/20/75)). The phosphoamidites dT-, dA$^{Pac}$-, dC$^{Ac}$—, dG$^{iPr-Pac}$, dA$^{Bz}$-, dC$^{BZ}$ and dG$^{DMF}$ were used following the manufacturers instructions (0.1 mol/L dry acetonitrile). The synthesized phosphoamidites 25D, 25L, 26α and 26β were used in 0.2 M solution in dry acetonitrile. The quality of each coupling step was monitored by measuring the conductivity of DMTr cleavage solutions. The synthesizer was programmed to yield oligomers carrying the terminal DMTr protective group "trityl-on". Table 1 lists the sequences of oligonucleotide probes synthesized according to the present invention.

TABLE 1

| Monomer | Entry | Sequence | SEQ ID No: |
|---|---|---|---|
| (L)-Serinol(TO) | 30A | 5'-G C C G T A TO A T A G C C G-3' | 1 |
| | 30T | 5'-G C C G T T TO T T A G C C G-3' | 2 |
| | 30C | 5'-G C C G T C TO C T A G C C G-3' | 3 |
| | 30G | 5'-G C C G T G TO G T A G C C G-3' | 4 |
| | 40 | 5'-A C A C C TO A C G G C G C-3' | 21 |
| (D)-Serinol(TO) | 31A | 5'-G C C G T A TO A T A G C C G-3' | 5 |
| | 31T | 5'-G C C G T T TO T T A G C C G-3' | 6 |
| | 31C | 5'-G C C G T C TO C T A G C C G-3' | 7 |
| | 31G | 5'-G C C G T G TO G T A G C C G-3' | 8 |
| | 41 | 5'-A C A C C TO A C G G C G C-3' | 22 |
| β-(D)-Carba-Desoxyribose(TO) | 32A | 5'-G C C G T A TO A T A G C C G-3' | 9 |
| | 32T | 5'-G C C G T T TO T T A G C C G-3' | 10 |
| | 32C | 5'-G C C G T C TO C T A G C C G-3' | 11 |
| | 32G | 5'-G C C G T G TO G T A G C C G-3' | 12 |
| α-(D)-Carba-Desoxyribose(T) | 33A | 5'-G C C G T A TO A T A G C C G-3' | 13 |
| | 33T | 5'-G C C G T T TO T T A G C C G-3' | 14 |
| | 33C | 5'-G C C G T C TO C T A G C C G-3' | 15 |
| | 33G | 5'-G C C G T G TO G T A G C C G-3' | 16 |
| | 43 | 5'-A A A A T G TO G G C A A A T A-3' | 24 |
| | 44 | 5'-A A A A T G G G G C A TO A T A-3' | 25 |

The probes 30-33 represented by SEQ ID No 1 to SEQ ID No 16 are directed against "theoretical" model DNA targets having SEQ ID No 17 to SEQ ID No 20. A second series of probes was targeted against biologically occurring gene segments (Table 1). The oligomers 40 and 41 represented by SEQ ID No: 21 and SEQ ID No: 22 were designed to recognize a segment of the human RAS gene, carrying a carcinogenic G12V mutation as shown by SEQ ID No: 23. The oligomers 43 and 44 SEQ ID No: 24 and SEQ ID No: 25 target a segment of the RNA genome of the Bovine Respiratory Syncytial Virus (RSV) as shown by SEQ ID No: 26.

EXAMPLE 13

DNA Work-Up and Purification

After synthesis the resulting CPGs were dried under reduced pressure for 1 h and then transferred to 2 mL eppendorf tubes. 1 mL of saturated aqueous NH$_4$OH was added and the tubes were shaken for 4 h at RT. Subsequently, the tubes were centrifuged and the supernatant was collected. The volatiles were evaporated by using a Uniequip Speed-vac Unijet II. The samples were then dissolved in 0.1 TEAA buffer (pH=7) and the crude product was further purified by RP- HPLC (gradient I). Afterwards, DMTr removal was induced through the addition of 50% AcOH aqueous solution over 30 min. The reaction mixtures were neutralized with NEt$_3$ and the crude product was again purified by RP-HPLC (gradient II). Afterwards, the resulting oligomers were concentrated to an overall volume of 0.5 mL and desalted using NAP-5 Sephadex columns of GE Healthcare or Amersham Biosciences. Finally the oligomers were freeze dried with a Christ LDC 1m lyophilizer. The residues were dissolved in water (Milli-Q-Pore) to reach a final concentration of 0.1 mM. Identity and purity was determined by using analytical RP-HPLC (gradient II) or HPLC (gradient III) and MALDI-TOF mass spectroscopy.

Semi preparative RP-HPLC was carried out on a 1105 HPLC System from Gilson, for analytical RP-HPLC a 1105 HPLC System of Gilson and a Acquity HPLC System of Waters were used. A UV-detector at a wavelength $\lambda=260$ nm and $\lambda=520$ nm was used for the detection. Semi preparative separations were carried out by using a Polaris C18 A 5μ (PN A 2000–250×100)-Column of Varian (Pore size 220 angstrom) at a flow rate of 4 mL/min at 55° C. Analytical HPLC was carried out by using a XBridg C18 5μ (250×046)-column of Waters (Pore size 130 angstrom) at a flow rate of 1 mL/min at 55° C. or a BEH 130 C18 1.7 μm (2.1×50)-column of Waters (pore size 130 angstrom) at a flow rate of 1 mL/min at 55° C.

As mobile phase a binary mixture of A (0.1 M TEAA buffer, pH=7, aq.) and B (acetonitrile) was used. All aqueous solutions were made of water of Milli-Q-Pore purity.
Gradient I: 0-1 min 3% B, 1-21 min 3% B→40% B
Gradient II: 0-1 min 3% B, 1-21 min 3% B→20% B
Gradient III: 0-4 min 3% B→20% B

EXAMPLE 14

MALDI-TOF Mass Spectroscopy

MALDI-TOF mass spectra were measured on a Voyager-DETM Pro Biospectrometry Workstation of PerSeptive Biosystems. For ionisation a nitrogen UV-laser with a wavelength of $\lambda=337$ nm was used. Acceleration voltage: 20.000 V, grid: 95%, guide wire: 0.025%, delay time: 100 ns. As matrix a solution of 2 parts of a solution of 50 mg 2',4',6'-trihydroxyacetophenone in 1 mL EtOH and 1 part of a solution of 50 mg diammonium citrate in 1 mL water (Milli-Q-Pore) was used.

EXAMPLE 15

Probe Analysis

For analysis of the probes extinction coefficient, MALDI-TOF mass spectra and retention time in HPLC were measured. Table 2 shows the results of the analysis together with the yields achieved by DNA synthesis

TABLE 2

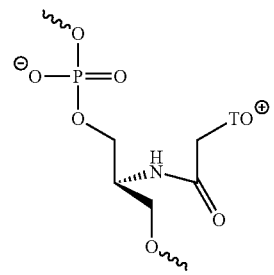

(D)-Serinol (TO)

| Nr | Sequence | Yield | $\epsilon_{260}$ (cm$^2$/mol) | m/z calc. | m/z found | R$_t$ Gr. II (min) |
|---|---|---|---|---|---|---|
| 31A | 5'-GCCGTA TO ATAGCCG-3' | 27.4% | 138.2 | 4444.1 | 4445.6 | 17.05 |
| 31T | 5'-GCCGTT TO TTAGCCG-3' | 18.1% | 134.4 | 4426.0 | 4428.6 | 17.23 |
| 31C | 5'-GCCGTC TO CTAGCCG-3' | 20.0% | 127.0 | 4396.0 | 4397.1 | 16.07 |
| 31G | 5'-GCCGTG TO GTAGCCG-3' | 20.1% | 134.2 | 4476.1 | 4477.7 | 15.60 |
| 41 | 5'-ACACC TO ACGGCGC-3' | 12.0% | 123.1 | 4084.8 | 4084.7 | 17.20 |

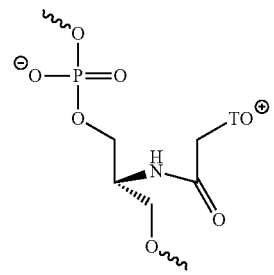

(L)-Serinol (TO)

| 30A | 5'-GCCGTA TO ATAGCCG-3' | 5.3% | 138.2 | 4444.1 | 4443.6 | 17.09 |
|---|---|---|---|---|---|---|
| 30T | 5'-GCCGTT TO TTAGCCG-3' | 1.0% | 134.4 | 4426.0 | 4425.9 | 17.54 |

TABLE 2-continued

| Nr | Sequence | Yield | $\varepsilon_{260}$ (cm²/mol) | m/z calc. | m/z found | $R_t$ Gr. II (min) |
|---|---|---|---|---|---|---|
| 30C | 5'-GCCGTC TO CTAGCCG-3' | 2.1% | 127.0 | 4396.0 | 4398.4 | 15.70 |
| 30G | 5'-GCCGTG TO GTAGCCG-3' | 2.1% | 134.2 | 4476.1 | 4478.9 | 15.89 |
| 40 | 5'-ACACC TO ACGGCGC-3' | 4.0% | 123.1 | 4084.8 | 4084.7 | 17.60 |

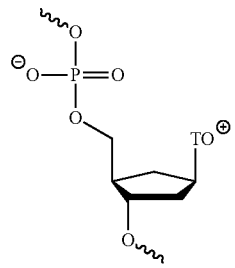

β-(D)-6'-C-Deoxyribose (TO)

| 32A | 5'-GCCGTA TO ATAGCCG-3' | 18.6% | 138.2 | 4427.1 | 4427.7 | 16.88 |
|---|---|---|---|---|---|---|
| 32T | 5'-GCCGTT TO TTAGCCG-3' | 18.0% | 134.4 | 4409.1 | 4410.3 | 17.25 |
| 32C | 5'-GCCGTC TO CTAGCCG-3' | 20.6% | 127.0 | 4379.0 | 4380.2 | 16.22 |
| 32G | 5'-GCCGTG TO GTAGCCG-3' | 18.5% | 134.2 | 4459.1 | 4460.2 | 15.53 |

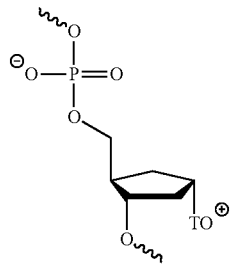

α-(D)-6'-C-Deoxyribose (TO)

| 33A | 5'-GCCGTA TO ATAGCCG-3' | 3.4% | 138.2 | 4427.1 | 4427.4 | 17.77 |
|---|---|---|---|---|---|---|
| 33T | 5'-GCCGTT TO TTAGCCG-3' | 3.8% | 134.4 | 4409.1 | 4406.0 | 17.85 |
| 33C | 5'-GCCGTC TO CTAGCCG-3' | 5.1% | 127.0 | 4379.0 | 4378.4 | 15.85 |
| 33G | 5'-GCCGTG TO GTAGCCG-3' | 3.8% | 134.2 | 4459.1 | 4458.8 | 15.27 |
| 43 | 5'-AAAAATG TO GGCAAATA-3' | 4.4% | 180.5 | 5109.6 | 5108.4 | 17.44 |
| 44 | 5'-AAAAATGGGCA TO ATA-3' | 6.1% | 177.4 | 5125.6 | 5124.7 | 18.90 |

EXAMPLE 16

Melting Analysis

Sensitivity of the probes according to the invention was tested in several hybridization experiments. The exchange of a nucleobase by a cyanine dye inevitably leads to the loss of hydrogen bonds within the formed probe-target complex. However, it was found that the affinity of the TO-labelled probes towards the target is not affected (Table 3). Surprisingly, the extraordinary stacking properties allow thiazole orange to compensate not only for the loss of hydrogen bonding, but even for the perturbations caused by the introduction of the modified pentose sugar or serinol backbone.

As described in examples 1 to 9, TO was attached to modified backbone moieties (2D, 2L, 3α and 3β). Thermal stability of the complexes formed with the probes according to the invention was compared to the thermal stability of an unmodified complex. As unmodified complex theoretical model DNA target (36) (SEQ ID No: 17) was hybridized to the perfect match probe (35) having SEQ ID No: 27. It was found that the complexes formed with the modified probes according to the invention show the same thermal stability than the unmodified complex. This is very surprising because the incorporation of (D)- or (L)-serinol(T) normally leads to a reduction of the complex stability of $\Delta T_m = -9°$ C. or $\Delta T_m = -12°$ C. Advantageously, thiazole orange provides compensation. The duplex 30A:36 (SEQ ID No: 1: SEQ ID No: 17) carrying the (L)-serinol(TO)-nucleotide is as stable as the unmodified duplex 35:36 (SEQ ID No: 27: SEQ ID No: 17). The (D)-serinol(TO)-nucleotide causes a minor destabilisation of $\Delta T_m = -4°$ C. (31A·36, (SEQ ID No: 5: SEQ ID No: 17). The complexes carrying TO linked to carba-cycles (32A·36 and 33A·36, SEQ ID No: 9: SEQ ID No: 17 and SEQ ID No: 13: SEQ ID No: 17) are as stable as unmodified duplex 35:36 (SEQ ID No: 27: SEQ ID No: 17). The variation of the neighbouring nucleobases adjacent to the TO-label showed an increase in thermal stability if an AT-basepair is exchanged by a GC-basepair. Table 3 shows the experimental results.

TABLE 3

Melting temperatures ($T_M$) of probe series 30-33 each with complementary DNA 36-39

| | |
|---|---|
| 5'-G C C G T X TOX T A G C C G-3' | (30X-33X, X = A, T, C, G) SEQ ID No: 1-16 |
| 5'-G C C G T A A A T A G C C G-3' | (35), SEQ ID No: 27 |
| 3'-C G G C A T T T A T C G G C-5' | (36), SEQ ID No: 17 |
| 3'-C G G C A A T A A T C G G C-5' | (37), SEQ ID No: 18 |
| 3'-C G G C A G T G A T C G G C-5' | (38), SEQ ID No: 19 |
| 3'-C G G C A C T C A T C G G C-5' | (39), SEQ ID No: 20 |

| Monomer | FIT-probe-target-DNA complex/$T_M$ | | | |
|---|---|---|---|---|
| β-(D)-Deoxyribose(A) | 35-36 | | | |
| | 55° C. | | | |
| L)-Serinol(TO) | 30A-36 | 30T-37 | 30C-38 | 30G-39 |
| | 55° C. | 57° C. | 65° C. | 61° C. |
| D)-Serinol(TO) | 31A-36 | 31T-37 | 31C-38 | 31G-39 |
| | 51° C. | 53° C. | 61° C. | 59° C. |
| β-(D)-Carba-Deoxyribose(TO) | 32A-36 | 32T-37 | 32C-38 | 32G-39 |
| | 53° C. | 56° C. | 63° C. | 59° C. |
| α-(D)-Carba-Deoxyribose(TO) | 33A-36 | 33T-37 | 33C-38 | 33G-39 |
| | 56° C. | 60° C. | 67° C. | 60° C. |

EXAMPLE 16

Fluorescence Measurement

Figure 7:
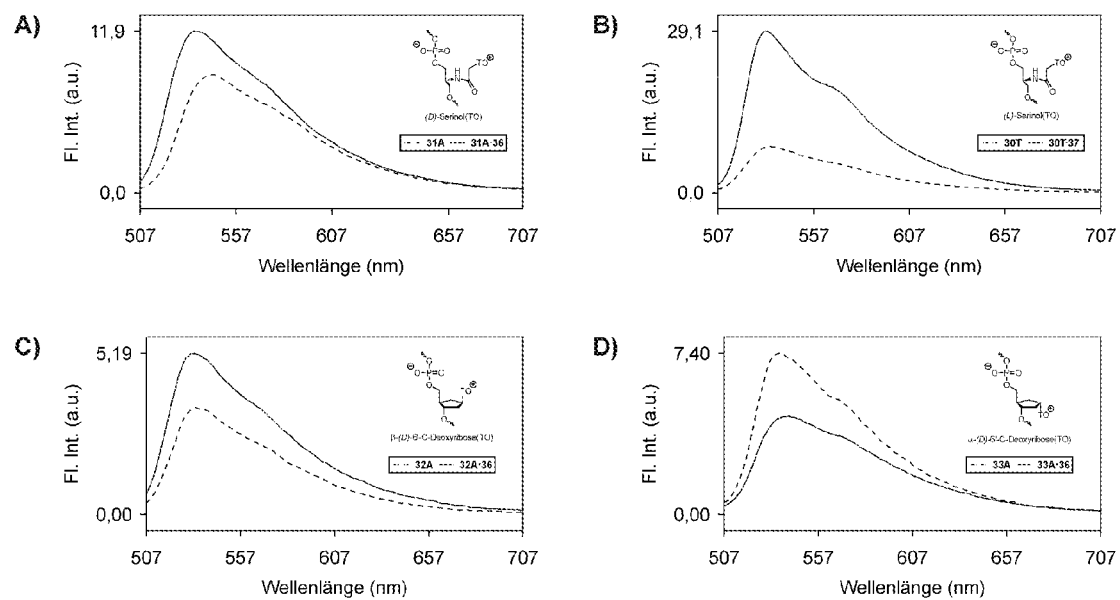
FIG. 7 shows change of fluorescence of the probe having (D)-Serinol(TO) (FIG. 7A), (L)-Serinol(TO) (FIG. 7B), β-(D)-Carba-2'-deoxyribose(TO) (FIG. 7C) and α-(D)-Carba-2'-deoxyribose(TO) (FIG. 7D), respectively, after adding the fully complementary DNA (for probe sequence see Tables 1 and 3)

Fluorescence emission spectra were measured prior to and after addition of fully complementary DNA. The hybridization-induced fluorescence enhancement ($E=I_{ds}/I_{ss}$; $I_{ds}$ and $I_{ss}$, fluorescence intensity of double strands and single strands, respectively) was calculated. FIG. 7 shows the fluorescence emission spectra of DNA-FIT-probes 30T (SEQ ID No: 2), 31A (SEQ ID No: 5), 32A (SEQ ID No: 9) and 33A (SEQ ID No: 13) before (dashed line) and after (solid line) addition of fully complementary DNA (36, SEQ ID No: 17 and 37, SEQ ID No: 18, respectively) at 25° C. FIG. 7 shows the results.

The single stranded probes show a maximum emission at 530 nm. Except for 33A an enhancement of the fluorescence signal at 525 nm was detected after addition of complementary DNA. Thus a positive fluorescence signal is achieved using the probes 30A, 31A and 32A and a negative fluorescence signal is achieved using the probe 33A. The decrease in fluorescence intensity using probe 33A is caused by the specific nucleic acid sequence. Table 4 shows the results of fluorescence enhancement of FIT-DNA-probe experiments using probes 30-33 according to the invention upon addition of fully complementary DNA 36-39 at 25° C., $\lambda_{Ex}$=495 nm, $Slit_{Ex}$=5, $Slit_{Em}$=2.5, 30-33, 36-39 1 µM in phosphate buffer (100 mM NaCl, 10 mM NaH$_2$PO$_4$, pH=7, 1 h degassed).

EXAMPLE 17

Homogeneous Detection of Single Mismatched DNA

Hybridization of 30T with fully complementary DNA 37 led, as mentioned above (Example 16), at 25° C. to a 3.64-fold enhancement of the TO-fluorescence (Table 4). Experiments were also performed at 50° C. and enhancement of TO-fluorescence was 5.3-fold. Furthermore, FIT-DNA 30T not only signals the presence of complementary DNA, but also allows discrimination between hybridization of fully complementary (37) represented by SEQ ID No: 18 and single mismatched DNA (37T, 37G, 37C) represented by SEQ ID No: 31-33. Experiments were repeated using FIT-DNA 30A (SEQ ID No: 1), the complementary DNA (36, SEQ ID No: 17) and single mismatched DNA (36A, 36G, 36C) represented by SEQ ID No: 28-30. Table 5 shows the probes and the DNA targets which were hybridized.

TABLE 4

| | |
|---|---|
| 5'-GCCGTXTOXTAGCCG-3' | (30X-33X, X = A, T, C, G) SEQ ID No: 1-16 |
| 3'-CGGCATTTATCGGC-5' | (36), SEQ ID No: 17 |
| 3'-CGGCAATAATCGGC-5' | (37), SEQ ID No: 18 |
| 3'-CGGCAGTGATCGGC-5' | (38), SEQ ID No: 19 |
| 3'-CGGCACTCATCGGC-5' | (39), SEQ ID No: 20 |

| Monomer | FIT-probe-target-DNA complex/ fluorescence enhancement, $E = I_{ds}/I_{ss}$ | | | |
|---|---|---|---|---|
| L)-Serinol(TO) | 30A-36 | 30T-37 | 30C-38 | 30G-39 |
| | 3.97 | 3.64 | 1.20 | 1.37 |
| D)-Serinol(TO) | 31A-36 | 31T-37 | 31C-38 | 31G-39 |
| | 1.36 | 0.81 | 0.85 | 0.97 |
| β-(D)-Carba-Deoxyribose(TO) | 32A-36 | 32T-37 | 32C-38 | 32G-39 |
| | 1.64 | 1.09 | 0.84 | 0.34 |
| α-(D)-Carba-Deoxyribose(TO) | 33A-36 | 33T-37 | 33C-38 | 33G-39 |
| | 0.60 | 0.45 | 0.41 | 0.58 |

TABLE 5

```
5'-GCCGTT TO TTAGCCG-3'  (30T)  SEQ ID No: 2      5'-GCCGTA TO ATAGCCG-3'  (30A)   SEQ ID No: 1
3'-CGGCAA T  AATCGGC-5'  (37)   SEQ ID No: 18     3'-CGGCAT T  TATCGGC-5'  (36)    SEQ ID No: 17
3'-CGGCAT T  AATCGGC-5'  (37T)  SEQ ID No: 31     3'-CGGCAA T  TATCGGC-5'  (36A)   SEQ ID No: 28
3'-CGGCAG T  AATCGGC-5'  (37G)  SEQ ID No: 32     3'-CGGCAG T  TATCGGC-5'  (36G)   SEQ ID No: 29
3'-CGGCAC T  AATCGGC-5'  (37C)  SEQ ID No: 33     3'-CGGCAC T  TATCGGC-5'  (36C)   SEQ ID No: 30
```

Discrimination of single mismatched duplexes against fully complementary duplexes experiments were performed by 25 and 50° C., using $\lambda_{ex}$ = 495 nm, $\lambda_{em}$ = 525 nm, $Slit_{Ex}$ = 5 nm and $Slit_{Em}$ = 2.5 1 µM of each probe 30T, 30A, 36, 36A-36C, 37, 37T-37C was used in phosphate buffer (100 mM NaCl, 10 mM NaH$_2$PO$_4$, pH = 7, 1 h degassed). Table 6 shows the results.

TABLE 6

|  | 30T-37 vs. 30T-37T | 30T-37G | 30T-37C | 30A-36 vs. 30A-36A | 30A-36G | 30A-36C |
| --- | --- | --- | --- | --- | --- | --- |
| 25° C. | 9.2 | 6.5 | 5.6 | 3.3 | 3.0 | 1.9 |
| 50° C. | 13.6 | 5.5 | 30.0 | 8.4 | 8.5 | 7.0 |

Figure 8:
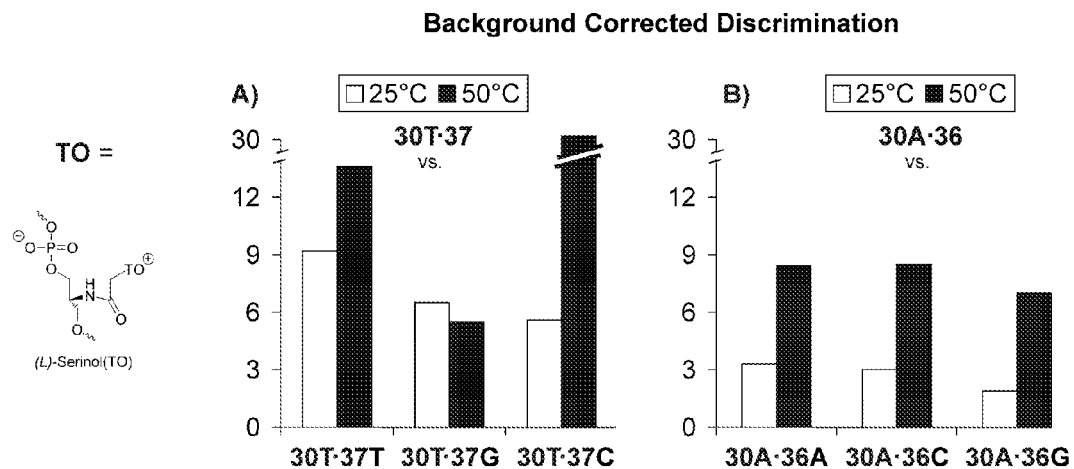
FIG. 8 shows the fluorescence enhancement of the probe having (L)-Serinol(TO) after perfect match hybridization compared to mismatch hybridization (for probe sequence see Table 5)

FIG. 8 shows the results graphically. Results were background corrected using D=[I$_{ds}$(match)−I$_{ss}$]/[I$_{ds}$(mismatch)−I$_{ss}$]. A) 30T·37 (match) vs. 30T·37T, 30T·37G and 30T·37C (mismatch) at 25 and 50° C. and B) 30A·36 (match) vs. 30A·36A, 30A·36G and 30A·36C (mismatch) at 25 and 50° C. For example, at 25° C. the background corrected discrimination of the TT-mismatch adjacent to TO against the AT-pair amounts to D(37/37T)=9.2, for the TG- and the TC-mismatch the discrimination amounts to D(37/37G)=6.5 and D(37/37C)=5.6, respectively (FIG. 8A, Table 6). The match/mismatch discrimination is even higher when the hybridization is performed at temperatures near the melting temperature of the mismatched duplexes. For example, the addition of matched DNA 37 to 30T at 50° C. led to a 30-fold higher background corrected fluorescence than the addition of single mismatched DNA 37C (FIG. 8A, Table 6). Likewise, hybridization of probe 30A with fully complementary DNA 36 resulted in a 2- to 4-fold (at 25° C.) or 7- to 9-fold (at 50° C.) higher background corrected fluorescence than the hybridization with mismatched targets 36A, 36C or 36G.

EXAMPLE 18

Homogeneous Detection of G12V Mutation in the Human RAS-Gene

For detecting the G12V mutation in the human RAS-gene probes 40 (SEQ ID No: 21) and 41 (SEQ ID No: 22) were hybridized with the mutated DNA 42 Mu (SEQ ID No: 23) and the unmutated, i.e. wild type, DNA 42 WT (SEQ ID No: 34). Probes 40 and 41 were fully complementary to the mutated gene. Thus, a mismatch is detected, if the probes 40 and 41 are hybridized to the wild type gene. Table 7 shows the probes used for hybridization experiments.

Figure 9:
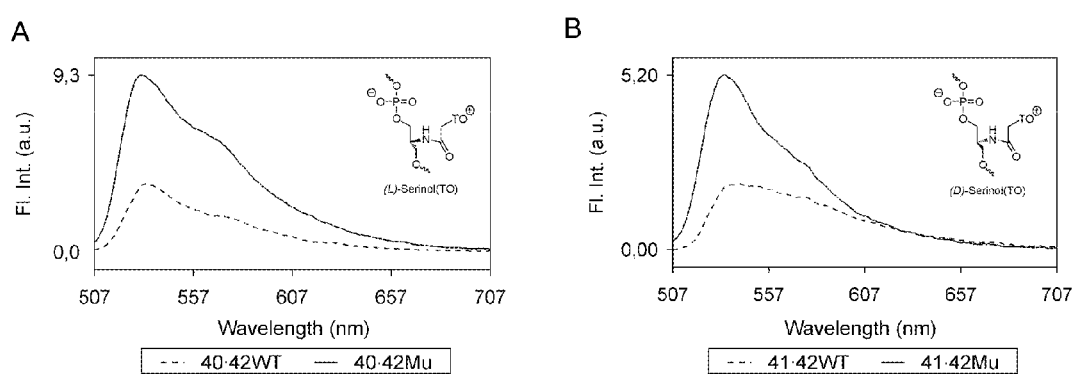
FIG. 9 shows the detection of mutated human RAS gene by fluorescence enhancement using the (L)-Serinol(TO)-probe and the (D)-Serinol(TO)-probe (for probe sequence see Table 7)

Hybridization experiments were performed at 250° C., using $\lambda_{ex}$=495 nm, $\lambda_{em}$=525 nm, $Slit_{Ex}$=5 nm and $Slit_{Em}$=2.5. 1 µM of each probe 40, 41, 42 Mu and 42 WT was used in phosphate buffer (100 mM NaCl, 10 mM NaH$_2$PO$_4$, pH=7, 1 h degassed). FIG. 9 shows the fluorescence spectra and Table 8 shows the fluorescence enhancement E and the background corrected discrimination of single mismatched duplexes versus fully complementary duplexes (40·42 Mu and 41·42 Mu (match, solid lines) vs. 40·42 WT and 41·42 WT (mismatch, dashed lines)).

TABLE 8

|  | 40 | | | 41 | | |
| --- | --- | --- | --- | --- | --- | --- |
|  | E | D | $T_M$ | E | D | $T_M$ |
| 42Mu | 3.1 | 3.3 | 64° C. | 2.7 | 3.3 | 60° C. |
| 42WT | — | | 59° C. | — | | 59° C. |

Hybridization of 40 with fully complementary DNA at 25° C. is signalled with a 3-fold enhancement of the TO-fluorescence. Even at this temperature, which is far below the $T_M$ of the mismatched probe-target-complex, the presence of the matched complex can be distinguished from the presence of the single mismatched complex, as the background corrected fluorescence of 40·42 Mu is raised by a factor of 3.3 compared to 40·42 WT (FIG. 9). The melting temperature of the fully complementary probe-target-complex 40·42 Mu amounts to $T_M$=64° C., the formation of the single mismatched complex 40·42 WT led to a reduced melting temperature by 5° C. of $T_M$=59° C. (Table 8). This, in turn, allows the conclusion, that the TO-modification in probe 40 does not affect the sequence specificity of probe-target recognition. It increases the match/mismatch discrimination when the hybridisation is preformed at higher temperature. Similar results were obtained when FIT-DNA-probe 41 was used in hybridization experiments (FIG. 9, Table 8).

EXAMPLE 19

Hybridization to a RNA-Segment of Bovine Respiratory Syncytial Virus (RSV)

To detect the RNA-segment of Bovine Respiratory Syncytial Virus (RSV) probes 43 (SEQ ID No: 24) and 44 (SEQ ID

TABLE 7

```
5'-A C A C C TO A C G G C G C-3'    (40: TO = (L)-serinol(TO)    (SEQ ID No: 21)

3'-T G T G G  C  T G C C G C G-5'   (41: TO = (D)-serinol(TO))   (SEQ ID No: 22)

(42 Mu) (SEQ ID No: 23)

3'-T G T G G  C  G G C C G C G-5'   (42 WT) (SEQ ID No: 34)
```

No: 25) were hybridized with the complementary virus RNA target 45 (SEQ ID No: 26). Table 9 shows the sequences of the probes.

TABLE 9

```
5'-A A A A A T G TO G G C A A A T A-3'     (43)  SEQ ID No: 24
5'-A A A A A T G G G G C A TO A T A-3'     (44)  SEQ ID No: 25

3'-U U U U U A C C C C G U U U A U-3'      (45)  SEQ ID No: 26
```

Figure 10:
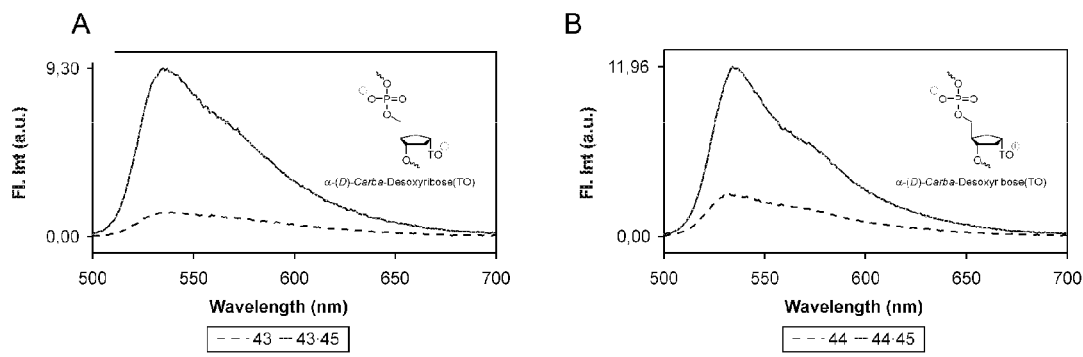
FIG. 10 shows the detection of RSV—RNA in a hybridization assay by fluorescence enhancement using the α-(D)-Carba-2'-deoxyribose(TO)-probe (for probe sequence see Table 9)

Hybridization of 43 to complementary RNA 45 at 25° C. led to a 7-fold enhancement of the TO-fluorescence. FIG. 10 shows the results. Fluorescence emission spectra of TO-DNA-conjugate 43 (A) and 44 (B) before (dashed line) and after (solid line) addition of target-RNA 45 were measured using $\lambda_{ex}$=495 nm, $Slit_{Ex}$=5 nm and $Slit_{Em}$=2.5. 1 µM of probe 43, 44, 45 were used in phosphate buffer (100 mM NaCl, 10 mM NaH$_2$PO$_4$, pH=7, 1 h degassed, 25° C.). The alternative FIT-DNA-probe 44 signalled the presence of RNA target 45 by means of a 3.5-fold enhancement of the TO-fluorescence.

EXAMPLE 20

Homogeneous Detection of a RNA-Segment of Bovine Respiratory Syncytial Virus (RSV)

Figure 11:
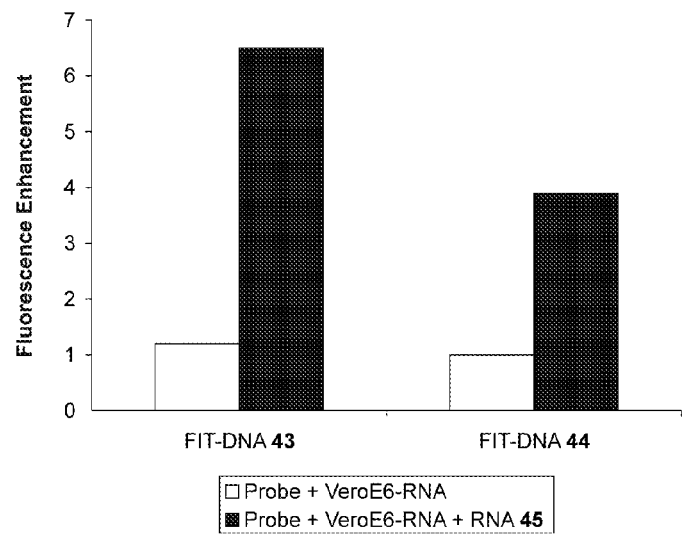
FIG. 11 shows the detection of RSV—RNA in a whole RNA-extract of VeroE6 cells by fluorescence enhancement using the α-(D)-Carba-2"-deoxyribose(TO)-probe (for probe sequence see Table 9).

After hybridization testes probes 43 and 44 were also used to detect the RNA-segment of bovine RSV in the presence of complex matrices. Therefore the RNA target was detected in whole cell RNA extracts. FIT-DNA 43 was incubated with whole cell RNA extract of VeroE6 cells (non target control or whole RNA matrix) and the TO-fluorescence was measured. The fluorescence emission of FIT-DNA 43 remained virtually unchanged. The same behaviour was observed when the extract was added to FIT-DNA 44. The target-RNA 45 was subsequently added the matrix and TO-fluorescence recorded again. The formation of the probe target complexes was accompanied by a 5.4-fold enhancement of the fluorescence of FIT-DNA 43. The emission of FIT-DNA 44 was enhanced by a factor of 3.9. FIG. 11 shows the fluorescence of FIT-DNA 43 and 44 at incubation with non target RNA (VeroE6-RNA) (white?) and fluorescence enhancement after additional incubation with target-RNA 45 (black?e). The selectivity is calculated as the ratio of target signal and non target signal (black bars/white bars). Fluorescence enhancement was calculated at T=30° C. using $\lambda_{ex}$=485 nm, $Slit_{Ex}$=20 nm, $\lambda_{em}$=530 nm and $Slit_{Em}$=10 nm, 60 mM of probe 43, 44, 3 ng/µL VeroE6-RNA, 2 µM RNA 45, in Tris buffer (100 mM Tris-HCl, 1 mM MgCl$_2$, pH=8, 1 h degassed) having a volume of 150 µL.

The invention claimed is:

1. A hybridization probe comprising at least one nucleoside analogue having the formula $$5'\text{-}(N1)_n\text{---}X_{t1}\text{-}NA\text{-}X_{t2}\text{-}(N2)_m\text{---}X_{t3}\text{-}[NA\text{-}X_{t4}\text{-}(N3)_o]_p\text{-}3',$$

wherein

N1, N2, N3 is identical or different being guanosine, cytidine, adenosine, thymidine, uracidine, inosine or a modification thereof, NA is a nucleoside analogue being a fluorescent artificial nucleobase linked to $C_1$ of a carba-pentose or a carba-hexose in α- or β-configuration or is a fluorescent artificial nucleobase directly bound to an amino acid nucleic acid (AANA) having one of the following structures:

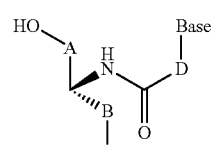   A

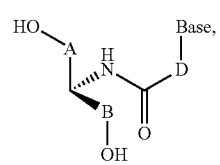   B wherein A, B and D are identical or different and represent a carbon, a substituted or unsubstituted $C_1$-$C_6$ alkyl group, wherein the substituent is an amino-group or a $C_1$-$C_6$ alkyl group, or an O or S,
n is an integer from 0 to 100,
m is an integer from 0 to 100,
o is an integer from 0 to 100,
p is an integer from 0 to 20
X is a linker group containing at least one phosphor atom and
t1, t2, t3, t4 is an integer from 0 to 5.

2. The hybridization probe according to claim 1, wherein the artificial nucleobase is a fluorescent DNA intercalator.

3. The hybridization probe according to claim 1, wherein the artificial nucleobase is thiazole orange (TO).

4. The hybridization probe according to claim 1, wherein
n is an integer from 0 to 20,
m is an integer from 0 to 20,
o is an integer from 0 to 20, and
p is an integer from 0 to 5.

5. The hybridization probe according to claim 1, wherein X is a mono-, di-, triphosphate, a mono-, di-, triphosphonate, a methyl phosphonate, a phosphorthioate or a phosphordithioate, a phosphorselenoate, an amide, a phosphoamide, a phosphoneamide or a carboxylic acid amide.

6. The hybridization probe according to claim 1, wherein the carba-pentose or a carba-hexose is a carba-furanose having formula (I)

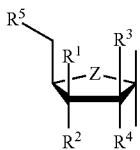

(I)

wherein Z is a $CH_2$-group, a CHR-group or a $CR_2$-group, whereby R is identical or different being a substituted or unsubstituted $C_1$-$C_6$ alkyl group, a substituted or unsubstituted phenyl group or a substituted or unsubstituted amino group, wherein the substituent is an amino-group, a $C_1$-$C_6$ alkyl or O or S,
$R^1$, $R^2$, $R^3$ and $R^4$ are identical or different being hydrogen, a hydroxyl-group, a halogen, a cyano group, an azido group, a substituted or unsubstituted $C_1$- to $C_6$-alkyl, a substituted or unsubstituted phenyl group, a substituted or unsubstituted amino group, wherein the substituent is an amino-group, a $C_1$-$C_6$ alkyl group or O or S, and
$R^5$ is a hydroxyl group or a substituted or unsubstituted amino- or thio-group, wherein the substituent is an amino group, a $C_1$-$C_6$ alkyl group or O or S.

7. The hybridization probe according to claim 6, wherein X is bound to $R^2$ and/or $R^5$.

8. The hybridization probe according to claim 1, wherein the AANA is Serinol, Threoninol or allo-Threoninol.

9. The hybridization probe according to claim 1, wherein the nucleoside analogue is α-(D)-6'-C-Deoxyribose(TO) or β-(D)-6'-C-Deoxyribose(TO), (L)-Serinol(TO), (D)-Serinol(TO), (L)-Threoninol(TO), (D)-Threoninol(TO), (L)-allo-Threoninol(TO), (D)-allo-Threoninol(TO), (L)-iso-Threoninol(TO), (D)-iso-Threoninol(TO), (L)-iso-allo-Threoninol(TO) or (D)-iso-allo-Threoninol(TO).

10. The hybridization probe according to claim 1, wherein
NA is α-(D)-6'-C-deoxyribose(TO) or β-(D)-6'-C-deoxyribose(TO), (L)-Serinol(TO) or (D)-Serinol(TO)
n is an integer from 0 to 20
m is an integer from 0 to 15 and
p is 0 and
X is a monophosphate and
t1, t2, t3, t4 are 1.

11. A method of production of the hybridization probe according to claim 1, comprising the step of producing the probe by solid phase synthesis, wherein the solid phase synthesis is phosphoamidite-synthesis.

12. A method for using a probe having at least one nucleoside analogue comprising the steps of:
providing at least one hybridization probe according to claim 1; and
performing a nucleic acid assay selected from the group consisting of PCR-reactions, fluorescence in situ hybridization (FISH) assays, in-vitro antisense or antigene assays, traceably knock-out or interference assays, DNA assays and RNA assays.

13. The method according to claim 12, further comprising:
providing at least two probes having different artificial nucleobases; and
performing a multiplex assay.

14. A kit comprising:
components needed for the method according to claim 12;
a means for performing said assays; and
a written description.

15. The hybridization probe according to claim 2, wherein the artificial nucleobase is a cyanine dye, an acridine dye, an ethidium dye, a proflavine dye, an daunomycine dye, an ellipticine dye, an anthracene dye, an quinacrine dye or 5'-, 6'-, 7'- or 8'-hydroxyquino line.

16. The hybridization probe according to claim 5, wherein X is a monophosphate.

17. The hybridization probe according to claim 6, wherein
Z is a CH2 group,
$R^1$, $R^2$, $R^3$ and $R^4$ are identical or different being a hydrogen, a fluoro group, a hydroxyl group, an amino group, a dimethyl amino group, a diethyl amino group, a carboxy group or a O-hydroxyalkyl group, an alkenyl group, or an alkinyl group, and
$R^5$ is OH.

18. The hybridization probe according to claim 1, wherein D of the AANA is an unsubstituted $C_1$ alkyl group.

19. The hybridization probe according to claim 1, wherein A and B of the AANA are a substituted or an unsubstituted $C_1$-$C_3$ group.

* * * * *